(12) United States Patent
Jiang et al.

(10) Patent No.: US 9,834,532 B2
(45) Date of Patent: Dec. 5, 2017

(54) STAT3 PATHWAY INHIBITORS AND CANCER STEM CELL INHIBITORS

(71) Applicant: BOSTON BIOMEDICAL, INC., Cambridge, MA (US)

(72) Inventors: Zhiwei Jiang, Stow, MA (US); Chiang Jia Li, Cambridge, MA (US); Wei Li, Wayland, MA (US); David Leggett, Milton, MA (US)

(73) Assignee: BOSTON BIOMEDICAL, INC., Cambridge, MA (US)

( * ) Notice: Subject to any disclaimer, the term of this patent is extended or adjusted under 35 U.S.C. 154(b) by 0 days.

(21) Appl. No.: 14/499,299

(22) Filed: Sep. 29, 2014

(65) Prior Publication Data
US 2015/0018410 A1    Jan. 15, 2015

Related U.S. Application Data

(63) Continuation of application No. 12/677,511, filed as application No. PCT/US2008/075848 on Sep. 10, 2008, now Pat. No. 8,877,803.

(60) Provisional application No. 60/971,144, filed on Sep. 10, 2007, provisional application No. 61/013,372, filed on Dec. 13, 2007.

(51) Int. Cl.
*C07D 307/92* (2006.01)
*C07D 333/74* (2006.01)
*A61K 31/38* (2006.01)

(52) U.S. Cl.
CPC ............ *C07D 307/92* (2013.01); *A61K 31/38* (2013.01); *C07D 333/74* (2013.01)

(58) Field of Classification Search
CPC .................................................. C07D 307/92
See application file for complete search history.

(56) References Cited

U.S. PATENT DOCUMENTS

| 6,337,346 B1 | 1/2002 | Lee et al. | |
| 6,828,337 B2 | 12/2004 | Belloni et al. | |
| 7,910,752 B2 * | 3/2011 | Tokuda | C07D 307/92 549/458 |

FOREIGN PATENT DOCUMENTS

| EP | 1860103 A1 | 11/2007 | |
| JP | 04139177 A * | 5/1992 | ........... C07D 307/86 |
| WO | 9962909 A2 | 12/1999 | |
| WO | 2004026253 A2 | 4/2004 | |
| WO | 2006098355 A1 | 9/2006 | |

OTHER PUBLICATIONS

Wermuth, Camille. "Molecular Variations Based on Isoteric Replacements." The Practice of Medicinal Chemistry. Academic Press, 1996. pp. 203-237.*
Han, Li. J. Nat. Prod. 2007, 70, 923-927.*
Byrn, Stephen. Solid-State Chemistry of Drugs, 2d, Chapter 11 Hydrates and Solvates/hydrates, 233-247, 233.*
Morissette, Sherry. Adv. Drug Delivery Rev. 2004, 56, 275-300.*
Mora, Linda. Cancer Research 62, 6659-6666 (2002).*
Leong, Paul. PNAS 100(7) 4138-4143 (2003).*
MedicineNet.com. http://www.medterms.com (2004).*
Peraza-Sanchez, et al. "Cytotoxic constituents of the roots of Ekmanianthe longiflora." J Nat Prod. Apr. 2000; 63(4):492-5.
Desmond, et al. "The synthetic furanonaphthoquinone induces growth arrest, apoptosis and differentiation in a variety of leukaemias and multiple myeloma cells." British Journal of Haematology. 131.4(2005):520-529.
Gafner, et al. "Antifunal and Antibacterial Naphthoquinones from Newbouldia Laevis Roots." Phytochemistry. 42.5 (1996):1315-1320.
Gormann, et al. "Furanonaphthoquinones, atraric acid and a benzofuran from the stem barks of Newbouldia laevis." Phytochemistry. 64.2(2004)583-587.
Itoigawa, et al. "Cancer cehmopreventive activity of naphthoquinones and their analogs from Avicennia plants." Cancer Letters. 174.2(2001):135-139.
Ogawa, et al. "Cytotoxic Activity toward KB Cells of 2-Substituted Naphtho[2,3-b]furan-4,9-diones and Their Related Compounds." Bioscience Biotechnology and Biochemistry. 70.4(2006):1009-1012.
Song, et al. "A low-molecular-weight compound discovered through virtual database screening inhibits Stat3 function in breast cancer cells." Proceedings of the National Academy of Sciences of the United States of America. 102.13 (2005):4700-4705.
STN Accession No. 1986:568912.
STN Accession No. 1992:245248.
STN Accession No. 1999:157137.
STN Accession No. 2002:33229.
Williams, et al. "Two New Cytotoxic Naphthoquinones from Mendoncia cowanii from the Rainforest of Madagascar." Planta Medica. 72.6(2006):564-566.
Yao, et al. "Experimental Study on the growth inhibition of bladder cancer cells by signal conduction blocker AG490." Journal of Clinical Urology. 21.5(2006):380-382.

\* cited by examiner

*Primary Examiner* — Golam M M Shameem
*Assistant Examiner* — Laura Daniel
(74) *Attorney, Agent, or Firm* — Boston Biomedical, Inc; Yi Liu, Esq.; Christopher D. Southgate, Esq.

(57) ABSTRACT

The present invention relates to a novel naphtho class of compounds as Stat3 pathway inhibitors and as cancer stem cell inhibitors; to methods of using such compounds to treat cancer; to methods of using such compounds to treat disorders in a mammal related to aberrant Stat3 pathway activity; to pharmaceutical compositions containing such compounds.

6 Claims, 6 Drawing Sheets

STAT3 PATHWAY INHIBITORS AND CANCER STEM CELL INHIBITORS

FIELD OF THE INVENTION

The present invention relates to a novel class of compounds as Stat3 pathway inhibitors, cancer stem cell inhibitors as well as cancer stem cell pathway inhibitors; to methods of using such compounds to treat cancer; to methods of using such compounds to treat disorders in a mammal related to aberrant Stat3 pathway activity; to synthesis and pharmaceutical compositions containing such compounds.

BACKGROUND OF THE INVENTION

Introduction of Stat3 Pathway

Stat3 is a member of the Stat family which are latent transcription factors activated in response to cytokines/growth factors to promote proliferation, survival, and other biological processes. Stat3 is activated by phosphorylation of a critical tyrosine residue mediated by growth factor receptor tyrosine kinases, Janus kinases, and/or the Src family kinases, etc. These kinases include but not limited to EGFR, JAKs, Abl, KDR, c-Met, Src, and Her2 [1]. Upon tyrosine phosphorylation, Stat3 forms homo-dimers and translocates to the nucleus, binds to specific DNA-response elements in the promoters of the target genes, and induces gene expression [2].

Importance of Stat3 pathway in Targeting Conventional Aspects of Cancers.

In normal cells, Stat3 activation is transient and tightly regulated, lasting from 30 minutes to several hours. However, Stat3 is found to be aberrantly active in a wide variety of human cancers, including all the major carcinomas as well as some hematologic tumors. Stat3 plays multiple roles in cancer progression. As a potent transcription regulator, it targets genes involved in cell cycle, cell survival, oncogenesis, tumor invasion, and metastasis, such as Bcl-xl, c-Myc, cyclin D1, Vegf, MMP-2, and survivin [3-8]. It is also a key negative regulator of tumor immune surveillance and immune cell recruitment [9-11].

Ablating Stat3 signaling by antisense, siRNA, dominant-negative form of Stat3, and/or blockade of tyrosine kinases causes cancer cell-growth arrest, apotosis, and reduction of metastasis frequency in vitro and/or in vivo [2, 4, 12, 13].

Importance of Stat3 pathway in Other Diseases.

Activation of Stat3 by various cytokines, such as Interleukin 6 (IL6) has been demonstrated in a number of autoimmune and inflammatory diseases. Recently, it has been revealed that the Stat3 pathway promotes pathologic immune responses through its essential role in generating TH17 T cell responses [14]. In addition, Stat3 pathway mediated inflammation is the common causative origin for atherosclerosis, peripheral vascular disease, coronary artery disease, hypertension, osteroprorosis, type 2 diabetes, and dementia. Therefore, Stat3 inhibitors may be used to prevent and treat autoimmune and inflammatory diseases as well as the other diseases listed above that are caused by inflammation.

Introduction of Cancer Stem Cells (CSCs).

Cancer stem cells (CSCs) are a sub-population of cancer cells (found within tumors or hematological cancers) that possess characteristics normally associated with stem cells. These cells are tumorigenic (tumor-forming), in contrast to the bulk of cancer cells, which are non-tumorigenic. In human acute myeloid leukemia the frequency of these cells is less than 1 in 10,000 [15]. There is mounting evidence that such cells exist in almost all tumor types. However, as cancer cell lines are selected from a sub-population of cancer cells that are specifically adapted to growth in tissue culture, the biological and functional properties of these cell lines can change dramatically. Therefore, not all cancer cell lines contain cancer stem cells.

CSCs have stem cell properties such as self-renewal and the ability to differentiate into multiple cell types. They persist in tumors as a distinct population and they give rise to the differentiated cells that form the bulk of the tumor mass and phenotypically characterize the disease. CSCs have been demonstrated to be fundamentally responsible for carcinogenesis, cancer metastasis, and cancer reoccurrence. CSCs are also often called tumor initiating cells, cancer stem-like cells, stem-like cancer cells, highly tumorigenic cells, or super malignant cells.

Clinical Implications of Cancer Stem Cells.

The existence of cancer stem cells has several implications in terms of cancer treatment and therapy. These include disease identification, selective drug targets, prevention of cancer metastasis and recurrence, treatment of cancer refractory to chemotherapy and/or radiotherapy, treatment of cancers inherently resistant to chemotherapy or radiotherapy and development of new strategies in fighting cancer.

The efficacy of cancer treatments are, in the initial stages of testing, often measured by the amount of tumor mass they kill off. As CSCs would form a very small proportion of the tumor and have markedly different biologic characteristics than their differentiated progeny, the measurement of tumor mass may not necessarily select for drugs that act specifically on the stem cells. In fact, cancer stem cells are radio-resistant and also refractory to chemotherapeutic and targeted drugs. Normal somatic stem cells are naturally resistant to chemotherapeutic agents—they have various pumps (such as MDR) that efflux drugs, higher DNA repair capability, and have a slow rate of cell turnover (chemotherapeutic agents naturally target rapidly replicating cells). Cancer stem cells, being the mutated counterparts of normal stem cells, may also have similar functions which allow them to survive therapy. In other words, conventional chemotherapies kill differentiated or differentiating cells, which form the bulk of the tumor that are unable to generate new cells. A population of cancer stem cells which gave rise to it could remain untouched and cause a relapse of the disease. Furthermore, treatment with chemotherapeutic agents may only leave chemotherapy-resistant cancer stem cells, so that the ensuing tumor will most likely also be resistant to chemotherapy. Cancer stem cells have also been demonstrated to be resistant to radiotherapy (XRT) [16, 17].

Since surviving cancer stem cells can repopulate the tumor and cause relapse, it would be possible to treat patients with aggressive, non-resectable tumors and refractory or recurrent cancers, as well as prevent the tumor metastasis and recurrence by selectively targeting cancer stem cells. Development of specific therapies targeted at cancer stem cells therefore holds hope for improvement of survival and quality of life of cancer patients, especially for sufferers of metastatic disease. The key to unlocking this untapped potential is the identification and validation of pathways that are selectively important for cancer stem cell self-renewal and survival. Though multiple pathways underlying tumorigenesis in cancer and in embryonic stem cells or adult stem cells have been elucidated in the past, no pathways have been reported for cancer stem cell self-renewal and survival.

Identification and Isolation of CSCs.

The methods on identification and isolation of cancer stem cells have been reported. The methods are used mainly to exploit the ability of CSCs to efflux drugs, or are based on the expression of surface markers associated with cancer stem cells.

CSCs are resistant to many chemotherapeutic agents, therefore it is not surprising that CSCs almost ubiquitously overexpress drug efflux pumps such as ABCG2 (BCRP-1) [18-22], and other ATP binding cassette (ABC) superfamily members [23, 24]. The side population (SP) technique, originally used to enrich hematopoetic and leukemic stem cells, was first employed to identify CSCs in the C6 glioma cell line [25]. This method, first described by Goodell et al., takes advantage of differential ABC transporter-dependent efflux of the fluorescent dye Hoechst 33342 to define a cell population enriched in CSCs [21, 26]. The SP is revealed by blocking drug efflux with verapamil, so that the SP is lost upon verapamil addition.

Efforts have also focused on finding specific markers that distinguish cancer stem cells from the bulk of the tumor. Markers originally associated with normal adult stem cells have been found to also mark cancer stem cells and co-segregate with the enhanced tumorigenicity of CSCs. The most commonly expressed surface markers by the cancer stem cells include CD44, CD133, and CD166 [27-33]. Sorting tumor cells based primarily upon the differential expression of these surface marker(s) have accounted for the majority of the highly tumorigenic CSCs described to date. Therefore, these surface markers are well validated for identification and isolation of cancer stem cells from the cancer cell lines and from the bulk of tumor tissues.

SUMMARY

We have identified Stat3 as a key cancer stem cell survival and self-renewal pathway. Therefore, Stat3 pathway inhibitors can kill cancer stem cells and inhibit cancer stem cell self-renewal.

In one aspect, the present invention provides a compound of formula I,

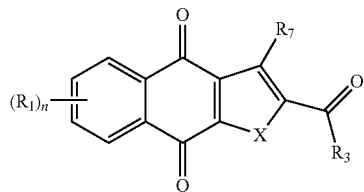

(I)

or an enantiomer, diastereomer, tautomer, or pharmaceutically acceptable salt or solvate thereof, wherein the symbols have the following meanings and are, for each occurrence, independently selected:

X is O or S;

$R_1$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_3$ is hydrogen, cyano, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, or $NR_bR_c$;

$R_7$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$ and $R_c$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and n is 1-4, provided that when $R_3$ is not $NR_bR_c$, then $R_7$ is not hydrogen and at least one of $R_1$ and $R_7$ is halogen, aryl, or substituted aryl.

In another aspect, the present invention provides a compound of formula II,

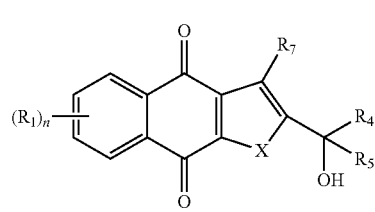

(II)

or an enantiomer, diastereomer, tautomer, or pharmaceutically acceptable salt or solvate thereof, wherein the symbols have the following meanings and are, for each occurrence, independently selected:

X is O or S;

$R_1$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, or $SR_a$;

$R_4$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, alkylaryl or substituted alkylaryl;

$R_5$ is hydrogen, alkyl or substituted alkyl, cycloalkyl or substituted cycloalkyl, aryl or substituted aryl, alkylaryl or substituted alkylaryl; optionally, $R_4$ and $R_5$ may be combined to form alkenyl or substituted alkenyl;

$R_7$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl; and n is 1-4, provided that at least one of $R_1$ and $R_7$ is halogen; or at least one of $R_1$, $R_4$, $R_5$ and $R_7$ is aryl or substituted aryl.

In yet another aspect, the present invention provides a compound of formula III,

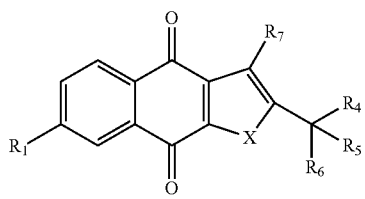

or an enantiomer, diastereomer, tautomer, or pharmaceutically acceptable salt or solvate thereof, wherein the symbols have the following meanings and are, for each occurrence, independently selected:

X is O or S;

$R_1$ is halogen;

$R_4$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, alkylaryl or substituted alkylaryl;

$R_5$ is hydrogen, alkyl or substituted alkyl, cycloalkyl or substituted cycloalkyl, aryl or substituted aryl, alkylaryl or substituted alkylaryl; optionally, $R_4$ and $R_5$ may be combined to form alkenyl or substituted alkenyl;

$R_6$ is hydrogen, alkyl or substituted alkyl, $OR_a$, $OC(=O)R_a$, or $SR_a$;

$R_7$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl; and n is 1-4.

In yet another aspect, the present invention provides a compound of formula IV,

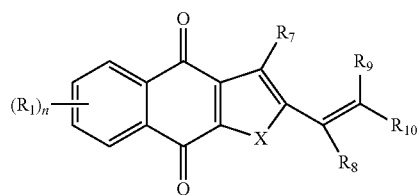

or an enantiomer, diastereomer, tautomer, or pharmaceutically acceptable salt or solvate thereof, wherein the symbols have the following meanings and are, for each occurrence, independently selected:

X is O or S;

$R_1$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_7$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_8$ is hydrogen, alkyl or substituted alkyl, cycloalkyl or substituted cycloalkyl, aryl or substituted aryl, alkylaryl or substituted alkylaryl;

$R_9$ and $R_{10}$ are each independently hydrogen, alkyl or substituted alkyl, cycloalkyl or substituted cycloalkyl, aryl or substituted aryl, heterocycle or substituted heterocycle, alkylaryl or substituted alkylaryl, alkylheteroaryl or substituted alkylheteroaryl; or $R_9$ and $R_{10}$ together with the carbon to which they are bonded optionally form cycloalkyl or substituted cycloalkyl, cycloalkenyl or substituted cycloalkenyl, heterocycle or substituted heterocycle;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl; and n is 1-4.

In yet another aspect, the present invention provides a compound of formula v,

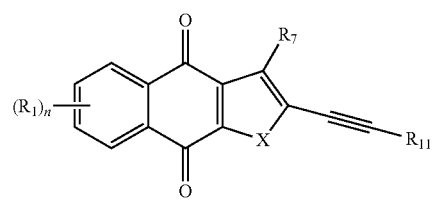

or an enantiomer, diastereomer, tautomer, or pharmaceutically acceptable salt or solvate thereof, wherein the symbols have the following meanings and are, for each occurrence, independently selected:

X is O or S;

$R_1$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_7$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_{11}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, alkylaryl or substituted alkylaryl, alkylheteroaryl or substituted alkylheteroaryl;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl; and n is 1-4.

In yet another aspect, the present invention provides a compound of formula VI, (VI)

or an enantiomer, diastereomer, tautomer, or pharmaceutically acceptable salt or solvate thereof, wherein the symbols have the following meanings and are, for each occurrence, independently selected:

X is O or S;

each $R_1$ is independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_3$ is hydrogen, cyano, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, or $NR_bR_c$;

$R_7$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$ and $R_c$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and provided that when $R_3$ is hydroxyl, alkyl, or substituted alkyl, then $R_1$ is halogen, aryl, or substituted aryl; and further provided that when $R_3$ is aryl or substituted aryl, then $R_7$ is not hydrogen, and further provided that 2-acetyl-7-chloro-naphtho[2,3-b]furan-4,9-dione and 2-acetyl-7-fluoro-naphtho[2,3-b]furan-4,9-dione are excluded.

In yet another aspect, the present invention provides a compound of formula VII:

(VII)

$R_1$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_3$ is hydrogen, cyano, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, or $NR_bR_c$;

$R_7$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$ and $R_c$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and n is 1-4, provided that when $R_3$ is not $NR_bR_c$, then $R_7$ is not hydrogen.

In another aspect, the present invention provides a pharmaceutical composition comprising a compound formulae I-VII as described hereinabove, or an enantiomer, diastereomer, tautomer, or a pharmaceutically-acceptable salt thereof, and a pharmaceutically-acceptable excipient, carrier, or diluent.

In yet another aspect, the present invention provides a method of treating cancer in a mammal, comprising administering to the mammal in need thereof a therapeutically effective amount of a compound of formulae I-VII as described hereinabove, or an enantiomer, diastereomer, tautomer, or pharmaceutically acceptable salt or solvate thereof. In one embodiment, the said cancer above is selected from breast cancer, head and neck cancer, lung cancer, ovarian cancer, pancreatic cancer, multiple myeloma, colorectal carcinoma, prostate cancer, melanoma, kaposi sarcoma, ewing's sarcoma, liver cancer, gastric cancer, medulloblastoma, brain tumors, leukemia. In another embodiment, the said cancer above is selected from lung cancer, breast cancer, cervical cancer, colon cancer, liver cancer, head and neck cancer, pancreatic cancer, gastric cancer, and prostate cancer.

In another aspect, the present invention provides a method of inhibiting or reducing unwanted Stat3 pathway activity with an effective amount of a compound of formulae I-VII as described hereinabove, or an enantiomer, diastereomer, tautomer, or pharmaceutically acceptable salt or solvate thereof.

In a further aspect, the present invention provides a method of treating a disorder associated with aberrant Stat3 pathway activity in a mammal, comprising administering to the mammal in need thereof a therapeutically effective amount of a compound of formulae I-VII as described hereinabove, or an enantiomer, diastereomer, tautomer, or pharmaceutically acceptable salt or solvate thereof. The aberrant Stat3 pathway activity can be identified by expression of phosphorylated Stat3 or its surrogate upstream or downstream regulators. In one embodiment, the said disorder is a cancer associated with aberrant Stat3 pathway activity which include but not limited to Breast cancer, head and neck cancer, lung cancer, ovarian cancer, pancreatic cancer, colorectal carcinoma, prostate cancer, renal cell carcinoma, melanoma, hepatocellular carcinomas, cervical cancer, sarcomas, brain tumors, gastric cancers, multiple myeloma, leukemia, and lymphomas. In another embodiment of the aspect, the said disorder is an autoimmune or inflammatory diseases associated with aberrant Stat3 pathway activity.

In another aspect, the present invention provides use of a compound of formula VIII:

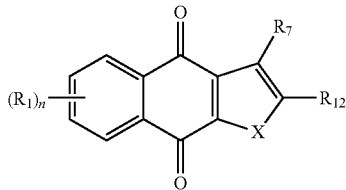

or an enantiomer, diastereomer, tautomer, or pharmaceutically acceptable salt or solvate thereof, wherein the symbols have the following meanings and are, for each occurrence, independently selected:

X is O or S;

$R_1$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_7$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_{12}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, alkylaryl or substituted alkylaryl, —C(=O)$R_3$, or —C(OH)$R_4R_5$;

$R_3$ is hydrogen, cyano, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, or $NR_bR_c$;

$R_4$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, alkylaryl or substituted alkylaryl;

$R_5$ is hydrogen, alkyl or substituted alkyl, cycloalkyl or substituted cycloalkyl, aryl or substituted aryl, alkylaryl or substituted alkylaryl; optionally, $R_4$ and $R_5$ may be combined to form alkenyl or substituted alkenyl;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$ and $R_c$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and n is 1-4, provided that 2-(1-hydroxyethyl)-naphtho [2,3-b]furan-4,9-dione, 2-acetyl-7-chloro-naphtho [2,3-b]furan-4,9-dione, 2-acetyl-7-fluoro-naphtho[2,3-b]furan-4,9-dione, 2-acetylnaphtho [2,3-b]furan-4,9-dione, and 2-ethyl-naphtho[2,3-b]furan-4,9-dione are excluded.

In a further aspect, the present invention provides a method of inhibiting cellular Stat3 pathway activity in a cell, comprising administering to the cell in need thereof an effective amount of a compound of formulae I-VIII as described herein such that at least undesired Stat3 pathway activity in the cell is reduced.

In one aspect, the present invention provides a method of treating a disorder associated with aberrant Stat3 pathway activity in a subject, the method comprising administering to the subject a therapeutically effective amount of a compound of formulae I-VIII as described herein.

In another aspect, the present invention provides a method of treating a patient, the method comprising: selecting a patient by aberrant Stat3 pathway activity; and administering to the patient a therapeutically effective amount of a compound of formulae I-VIII as described herein.

In yet another aspect, the present invention provides a method of treating a patient tested to have cancer expressing aberrant Stat3 pathway activity by administering to the patient a therapeutically effective amount of a compound of formulae I-VIII as described herein.

In yet another aspect, the present invention provides a method of inhibiting a cancer stem cell survival and/or self-renewal, the method comprising administering to a cancer stem cell with an effective amount of a compound of formulae I-VIII as described herein.

In yet another aspect, the present invention provides a method of treating a subject for cancer refractory to a standard regimen of treatment, the method comprising administering the subject a therapeutically effective amount of a compound of formulae I-VIII as described herein.

In yet another aspect, the present invention provides a method of treating relapsed cancer in a subject, the method comprising administering the subject a therapeutically effective amount of a compound of formulae I-VIII as described herein.

In yet another aspect, the present invention provides a method of treating or preventing cancer metastasis in a subject, the method comprising administering the subject a therapeutically effective amount of a compound of formulae I-VIII as described herein.

In yet another aspect, the present invention provides a method of treating a cancer in a subject, the method comprising administering the subject a therapeutically effective amount of formulae I-VIII as described herein.

Other aspects and embodiments of the present invention are set forth or will be readily apparent from the following detailed description of the invention.

DETAILED DESCRIPTION

A. Definitions

Figure 1:
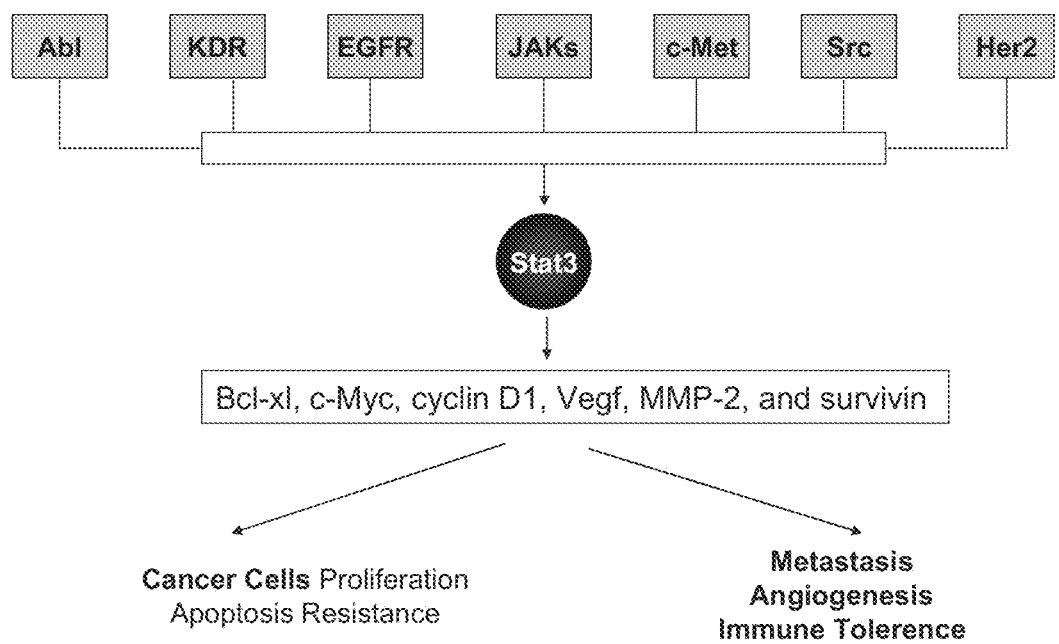
FIG. 1 shows the Stat3 pathway in cancer.
Figure 2:
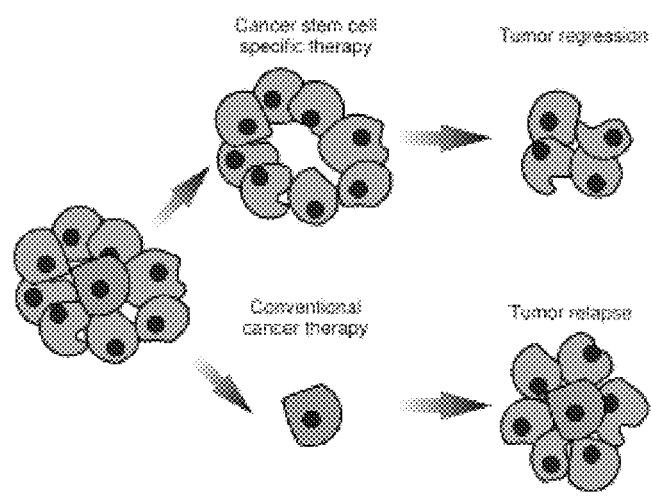
FIG. 2 shows the cancer stem cell specific and conventional cancer therapies.

The following are definitions of terms used in the present specification. The initial definition provided for a group or term herein applies to that group or term throughout the present specification individually or as part of another group, unless otherwise indicated.

The terms "alkyl" and "alk" refers to a straight or branched chain alkane (hydrocarbon) radical containing from 1 to 12 carbon atoms, preferably 1 to 6 carbon atoms. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. The term "$C_1$-$C_4$ alkyl" refers to a straight or branched chain alkane (hydrocarbon) radical containing from 1 to 4 carbon atoms, such as methyl, ethyl, propyl, isopropyl, n-butyl, t-butyl, and isobutyl. "Substituted alkyl" refers to an alkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_e$, $NR_bS(=O)_2R_e$, $NR_bP(=O)_2R_e$, $S(=O)_2NR_bR_e$, $P(=O)_2NR_bR_e$, $C(=O)OR_d$, $C(=O)R_a$, $C(=O)NR_bR_e$, $OC(=O)R_a$, $OC(=O)NR_bR_e$, $NR_bC(=O)OR_e$, $NR_dC(=O)NR_bR_e$, $NR_dS(=O)_2NR_bR_e$, $NR_dP(=O)_2NR_bR_e$, $NR_bC(=O)R_a$, or $NR_bP(=O)_2R_e$, wherein $R_a$ is hydrogen, alkyl, cycloalkyl, alkenyl, cycloalkenyl, alkynyl, heterocycle, or aryl; $R_b$, $R_c$ and $R_d$ are independently hydrogen, alkyl, cycloalkyl, heterocycle, aryl, or said $R_b$ and $R_c$ together with the N to which they are bonded optionally form a heterocycle or substituted heterocycle; and $R_e$ is alkyl, cycloalkyl, alkenyl, cycloalkenyl, alkynyl, heterocycle, or aryl. In the aforementioned exemplary substitutents, groups such as alkyl, cycloalkyl, alkenyl, alkynyl, cycloalkenyl, heterocycle and aryl can themselves be optionally substituted.

The term "alkenyl" refers to a straight or branched chain hydrocarbon radical containing from 2 to 12 carbon atoms and at least one carbon-carbon double bond. Exemplary such groups include ethenyl or allyl. "Substituted alkenyl" refers to an alkenyl group substituted with one or more substituents, preferably 1 to 4 substituents, at any available point of attachment. Exemplary substituents include, but are not limited to, alkyl or substituted alkyl, as well as those groups recited above as exemplary alkyl substituents. The exemplary substitutents can themselves be optionally substituted.

The term "alkynyl" refers to a straight or branched chain hydrocarbon radical containing from 2 to 12 carbon atoms and at least one carbon to carbon triple bond. Exemplary such groups include ethynyl. "Substituted alkynyl" refers to an alkynyl group substituted with one or more substituents, preferably 1 to 4 substituents, at any available point of attachment. Exemplary substituents include, but are not limited to, alkyl or substituted alkyl, as well as those groups recited above as exemplary alkyl substituents. The exemplary substitutents can themselves be optionally substituted.

The term "cycloalkyl" refers to a fully saturated cyclic hydrocarbon group containing from 1 to 4 rings and 3 to 8 carbons per ring. Exemplary such groups include cyclopropyl, cyclobutyl, cyclopentyl, cyclohexyl, cycloheptyl, etc. "Substituted cycloalkyl" refers to a cycloalkyl group substituted with one or more substituents, preferably 1 to 4 substituents, at any available point of attachment. Exemplary substituents include, but are not limited to, nitro, cyano, alkyl or substituted alkyl, as well as those groups recited above as exemplary alkyl substituents. The exemplary substitutents can themselves be optionally substituted. Exemplary substituents also include spiro-attached or fused cylic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substitutents can themselves be optionally substituted.

The term "cycloalkenyl" refers to a partially unsaturated cyclic hydrocarbon group containing 1 to 4 rings and 3 to 8 carbons per ring. Exemplary such groups include cyclobutenyl, cyclopentenyl, cyclohexenyl, etc. "Substituted cycloalkenyl" refers to a cycloalkenyl group substituted with one more substituents, preferably 1 to 4 substituents, at any available point of attachment. Exemplary substituents include but are not limited to nitro, cyano, alkyl or substituted alkyl, as well as those groups recited above as exemplary alkyl substituents. The exemplary substitutents can themselves be optionally substituted. Exemplary substituents also include spiro-attached or fused cylic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "aryl" refers to cyclic, aromatic hydrocarbon groups that have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably 1 to 3 substituents, at any point of attachment. Exemplary substituents include, but are not limited to, nitro, cycloalkyl or substituted cycloalkyl, cycloalkenyl or substituted cycloalkenyl, cyano, alkyl or substituted alkyl, as well as those groups recited above as exemplary alkyl substituents. The exemplary substitutents can themselves be optionally substituted. Exemplary substituents also include fused cylic groups, especially fused cycloalkyl, fused cycloalkenyl, fused heterocycle, or fused aryl, where the aforementioned cycloalkyl, cycloalkenyl, heterocycle and aryl substituents can themselves be optionally substituted.

The terms "heterocycle" and "heterocyclic" refer to fully saturated, or partially or fully unsaturated, including aromatic (i.e., "heteroaryl") cyclic groups (for example, 4 to 7 membered monocyclic, 7 to 11 membered bicyclic, or 8 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, benzo[d][1,3]dioxolyl, 2,3-dihydrobenzo[b][1,4]dioxinyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like. Thiazole?

"Substituted heterocycle" and "substituted heterocyclic" (such as "substituted heteroaryl") refer to heterocycle or heterocyclic groups substituted with one or more substituents, preferably 1 to 4 substituents, at any available point of attachment. Exemplary substituents include, but are not limited to, cycloalkyl or substituted cycloalkyl, cycloalkenyl or substituted cycloalkenyl, nitro, oxo (i.e., =O), cyano, alkyl or substituted alkyl, as well as those groups recited above as exemplary alkyl substituents. The exemplary substitutents can themselves be optionally substituted. Exemplary substituents also include spiro-attached or fused cylic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The terms "halogen" or "halo" refer to chlorine, bromine, fluorine or iodine.

The term "carbocyclic" refers to aromatic or non-aromatic 3 to 7 membered monocyclic and 7 to 11 membered bicyclic groups, in which all atoms of the ring or rings are carbon atoms. "Substituted carbocyclic" refers to a carbocyclic group substituted with one or more substituents, preferably 1 to 4 substituents, at any available point of attachment. Exemplary substituents include, but are not limited to, nitro, cyano, $OR_a$, wherein $R_a$ is as defined hereinabove, as well as those groups recited above as exemplary cycloalkyl substituents. The exemplary substitutents can themselves be optionally substituted.

The term "pharmaceutically-acceptable excipient, carrier, or diluent" as used herein means a pharmaceutically-acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

Unless otherwise indicated, any heteroatom with unsatisfied valences is assumed to have hydrogen atoms sufficient to satisfy the valences.

The compounds of the present invention may form salts which are also within the scope of this invention. Reference to a compound of the present invention herein is understood to include reference to salts thereof, unless otherwise indicated. The term "salt(s)", as employed herein, denotes acidic and/or basic salts formed with inorganic and/or organic acids and bases. In addition, when a compound of the present invention contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the present invention may be formed, for example, by reacting a compound I, II or III with an amount of acid or base, such as an equivalent amount, in a medium such as one in which the salt precipitates or in an aqueous medium followed by lyophilization.

The compounds of the present invention which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of the present invention which contain an acidic moiety, such but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl) ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Solvates of the compounds of the invention are also contemplated herein. Solvates of the compounds of the present invention include, for example, hydrates.

Compounds of the present invention, and salts thereof, may exist in their tautomeric form (for example, as an amide or imino ether). All such tautomeric forms are contemplated herein as part of the present invention.

All stereoisomers of the compounds of the present invention (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

Compounds of the present invention are, subsequent to their preparation, preferably isolated and purified to obtain a composition containing an amount by weight equal to or greater than 99% ("substantially pure" compound I), which is then used or formulated as described herein.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclic rings.

Throughout the specifications, groups and substituents thereof may be chosen to provide stable moieties and compounds.

B. Compounds

In one aspect, the present invention provides a compound of formula I,

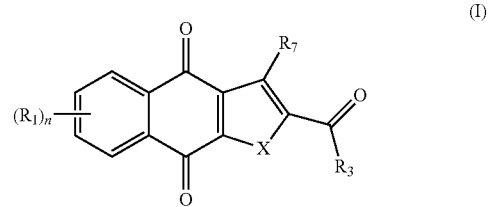

or an enantiomer, diastereomer, tautomer, or pharmaceutically acceptable salt or solvate thereof, wherein the symbols have the following meanings and are, for each occurrence, independently selected:

X is O or S;

$R_1$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_3$ is hydrogen, cyano, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, or $NR_bR_c$;

$R_7$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$ and $R_c$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and n is 1-4, provided that when $R_3$ is not $NR_bR_c$, then $R_7$ is not hydrogen and at least one of $R_1$ and $R_7$ is halogen, aryl, or substituted aryl.

In certain embodiments, the present invention provides a compound selected from the group consisting of:

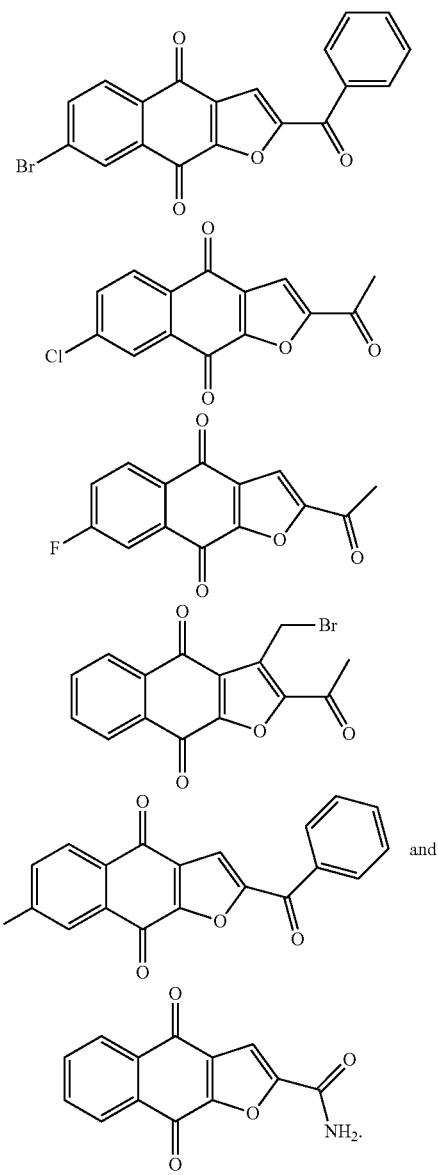

In certain other embodiments, the present invention provides a compound selected from the group consisting of:

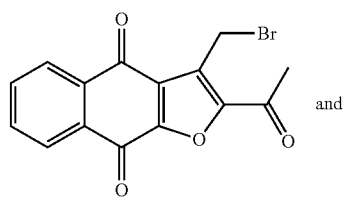

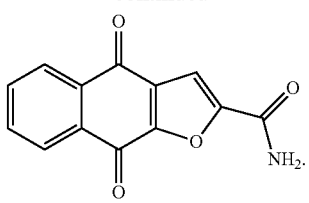

In another aspect, the present invention provides a compound of formula II,

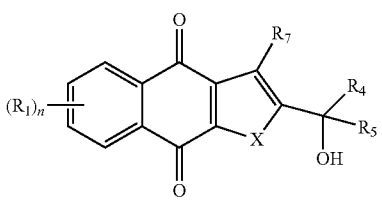

(II)

or an enantiomer, diastereomer, tautomer, or pharmaceutically acceptable salt or solvate thereof, wherein the symbols have the following meanings and are, for each occurrence, independently selected:

X is O or S;

$R_1$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, or $SR_a$;

$R_4$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, alkylaryl or substituted alkylaryl;

$R_5$ is hydrogen, alkyl or substituted alkyl, cycloalkyl or substituted cycloalkyl, aryl or substituted aryl, alkylaryl or substituted alkylaryl; optionally, $R_4$ and $R_5$ may be combined to form alkenyl or substituted alkenyl;

$R_7$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl; and n is 1-4, provided that at least one of $R_1$ and $R_7$ is halogen; or at least one of $R_1$, $R_4$, $R_5$ and $R_7$ is aryl or substituted aryl.

In certain embodiments, the compound of formula II is selected from the group consisting of:

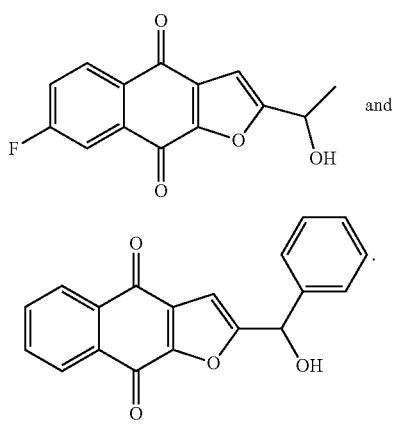

In yet another aspect, the present invention provides a compound of formula III,

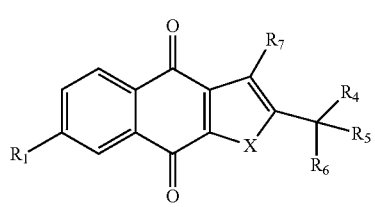

or an enantiomer, diastereomer, tautomer, or pharmaceutically acceptable salt or solvate thereof, wherein the symbols have the following meanings and are, for each occurrence, independently selected:

X is O or S;

$R_1$ is halogen;

$R_4$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, alkylaryl or substituted alkylaryl;

$R_5$ is hydrogen, alkyl or substituted alkyl, cycloalkyl or substituted cycloalkyl, aryl or substituted aryl, alkylaryl or substituted alkylaryl; optionally, $R_4$ and $R_5$ may be combined to form alkenyl or substituted alkenyl;

$R_6$ is hydrogen, alkyl or substituted alkyl, $OR_a$, $OC(=O)R_a$, or $SR_a$;

$R_7$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl; and n is 1-4.

In certain embodiments, the compound of formula III is

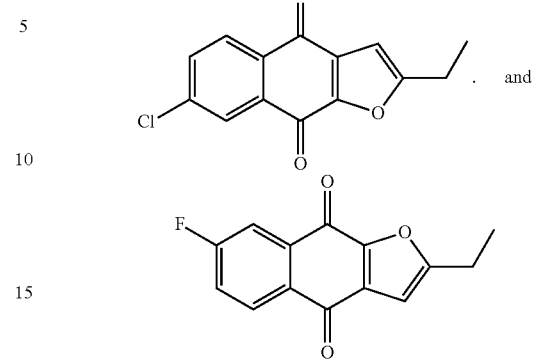

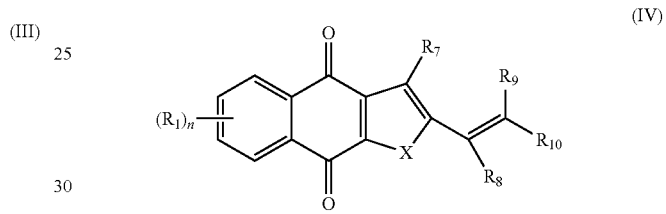

In yet another aspect, the present invention provides a compound of formula IV, or an enantiomer, diastereomer, tautomer, or pharmaceutically acceptable salt or solvate thereof, wherein the symbols have the following meanings and are, for each occurrence, independently selected:

X is O or S;

$R_1$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_7$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_8$ is hydrogen, alkyl or substituted alkyl, cycloalkyl or substituted cycloalkyl, aryl or substituted aryl, alkylaryl or substituted alkylaryl;

$R_9$ and $R_{10}$ are each independently hydrogen, alkyl or substituted alkyl, cycloalkyl or substituted cycloalkyl, aryl or substituted aryl, heterocycle or substituted heterocycle, alkylaryl or substituted alkylaryl, alkylheteroaryl or substituted alkylheteroaryl; or $R_9$ and $R_{10}$ together with the carbon to which they are bonded optionally form cycloalkyl or substituted cycloalkyl, cycloalkenyl or substituted cycloalkenyl, heterocycle or substituted heterocycle;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl; and n is 1-4.

In certain embodiments, the compound of formula IV is selected from the group consisting of:

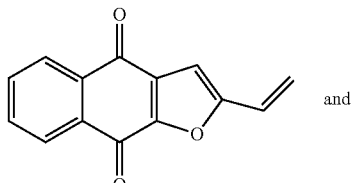 and

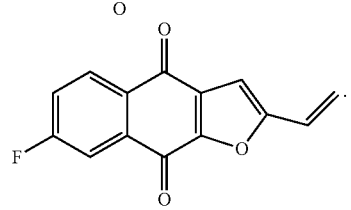

In yet another aspect, the present invention provides a compound of formula V,

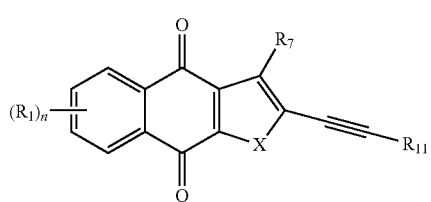

or an enantiomer, diastereomer, tautomer, or pharmaceutically acceptable salt or solvate thereof, wherein the symbols have the following meanings and are, for each occurrence, independently selected:

X is O or S;

$R_1$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_7$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_{11}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, alkylaryl or substituted alkylaryl, alkylheteroaryl or substituted alkylheteroaryl;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl; and n is 1-4.

In yet another aspect, the present invention provides a compound of formula VI,

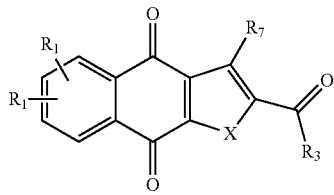

or an enantiomer, diastereomer, tautomer, or pharmaceutically acceptable salt or solvate thereof, wherein the symbols have the following meanings and are, for each occurrence, independently selected:

X is O or S;

each $R_1$ is independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_3$ is hydrogen, cyano, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, or $NR_bR_c$;

$R_7$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$ and $R_c$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and provided that when $R_3$ is hydroxyl, alkyl, or substituted alkyl, then $R_1$ is halogen, aryl, or substituted aryl;

further provided that when $R_3$ is aryl or substituted aryl, then $R_7$ is not hydrogen, and further provided that 2-acetyl-7-chloro-naphtho[2,3-b]furan-4,9-dione and 2-acetyl-7-fluoro-naphtho[2,3-b]furan-4,9-dione are excluded.

In certain embodiments, the present invention provides a compound selected from the group consisting of:

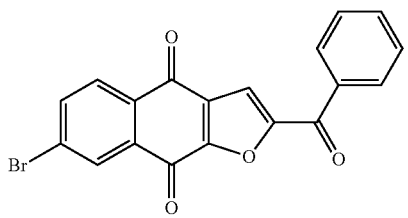

-continued

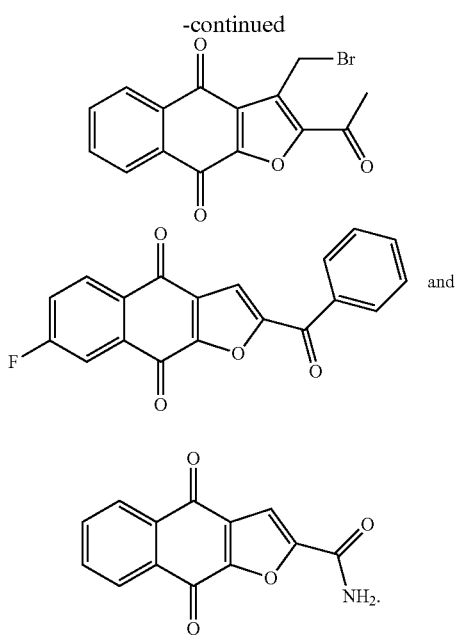

In yet another aspect, the present invention provides a compound of formula VII:

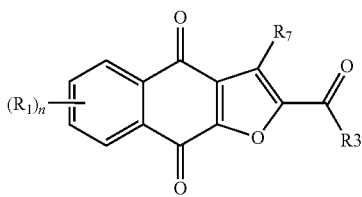

(VII)

R₁ is hydrogen, halogen, cyano, nitro, CF₃, OCF₃, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, or SR$_a$;

R₃ is hydrogen, cyano, CF₃, OCF₃, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, or NR$_b$R$_c$;

R₇ is hydrogen, halogen, cyano, nitro, CF₃, OCF₃, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, or SR$_a$;

R$_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

R$_b$ and R$_c$ are independently hydrogen, alkyl or substituted alkyl, cycloalkyl or substituted cycloalkyl, heterocycle or substituted heterocycle, or aryl or substituted aryl, or said R$_b$ and R$_c$ together with the N to which they are bonded optionally form a heterocycle or substituted heterocycle; and n is 1-4, provided that when R₃ is not NR$_b$R$_c$, then R₇ is not hydrogen.

In yet another aspect, the present invention provides a compound of formula VIII:

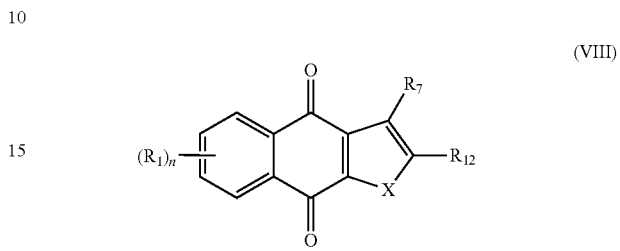

(VIII)

or an enantiomer, diastereomer, tautomer, or pharmaceutically acceptable salt or solvate thereof, wherein the symbols have the following meanings and are, for each occurrence, independently selected:

X is O or S;

R₁ is hydrogen, halogen, cyano, nitro, CF₃, OCF₃, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, or SR$_a$;

R₇ is hydrogen, halogen, cyano, nitro, CF₃, OCF₃, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, or SR$_a$;

R₁₂ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, alkylaryl or substituted alkylaryl, —C(=O)R₃, or —C(OH)R₄R₅;

R₃ is hydrogen, cyano, CF₃, OCF₃, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, or NR$_b$R$_c$;

R₄ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, alkylaryl or substituted alkylaryl;

R₅ is hydrogen, alkyl or substituted alkyl, cycloalkyl or substituted cycloalkyl, aryl or substituted aryl, alkylaryl or substituted alkylaryl; optionally, R₄ and R₅ may be combined to form alkenyl or substituted alkenyl;

R$_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

R$_b$ and R$_c$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and n is 1-4;

provided that 2-(1-hydroxyethyl)-naphtho [2,3-b]furan-4,9-dione, 2-acetyl-7-chloro-naphtho [2,3-b]furan-4,9-dione, 2-acetyl-7-fluoro-naphtho [2,3-b]furan-4,9-dione, 2-acetylnaphtho [2,3-b]furan-4,9-dione, and 2-ethyl-naphtho [2,3-b]furan-4,9-dione are excluded.

In certain embodiments, the compound of formula VIII is selected from the group consisting of:

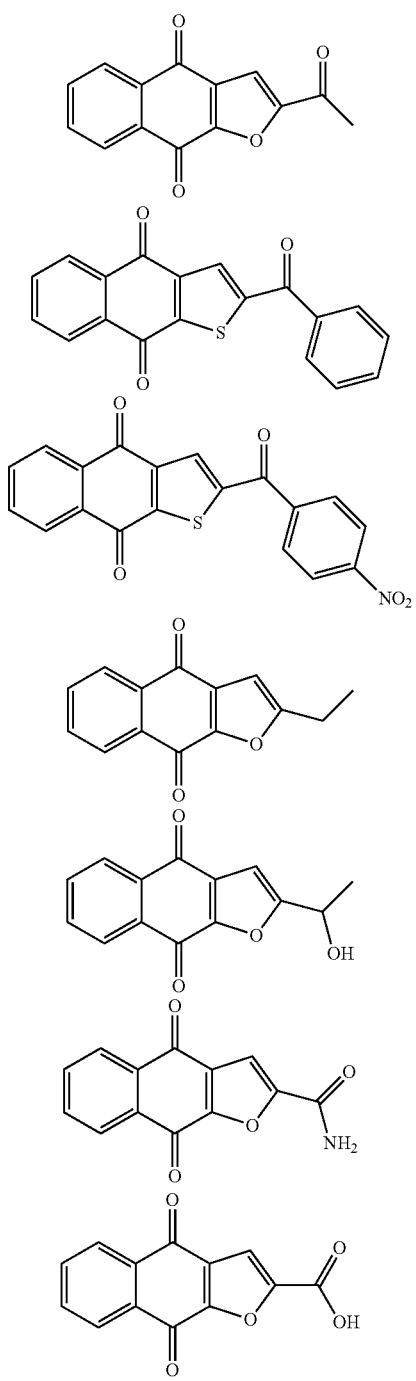
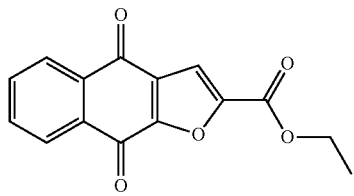
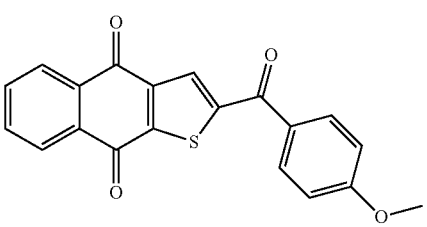
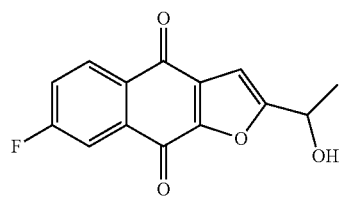
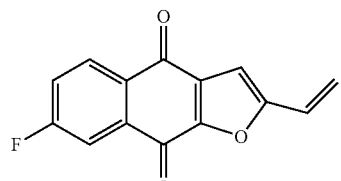
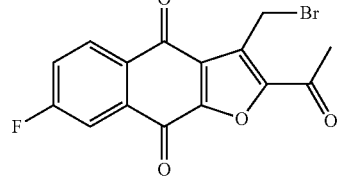
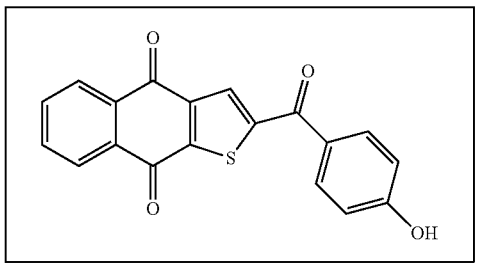
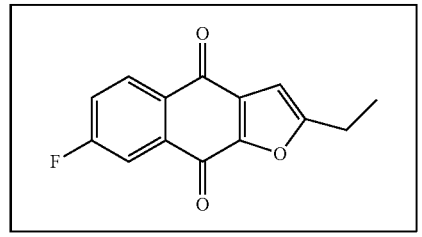

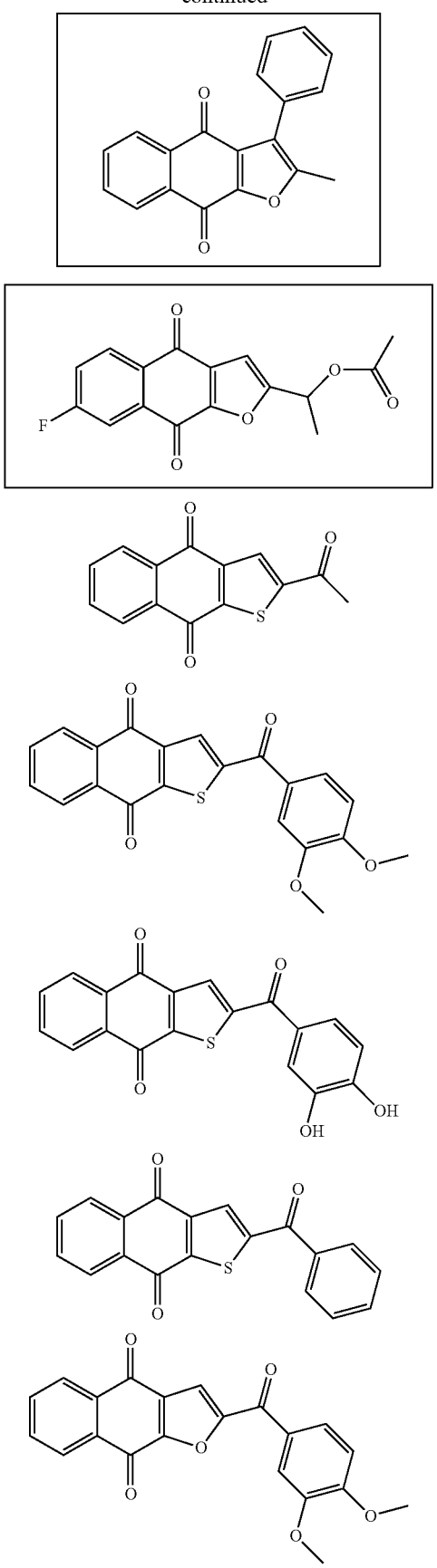
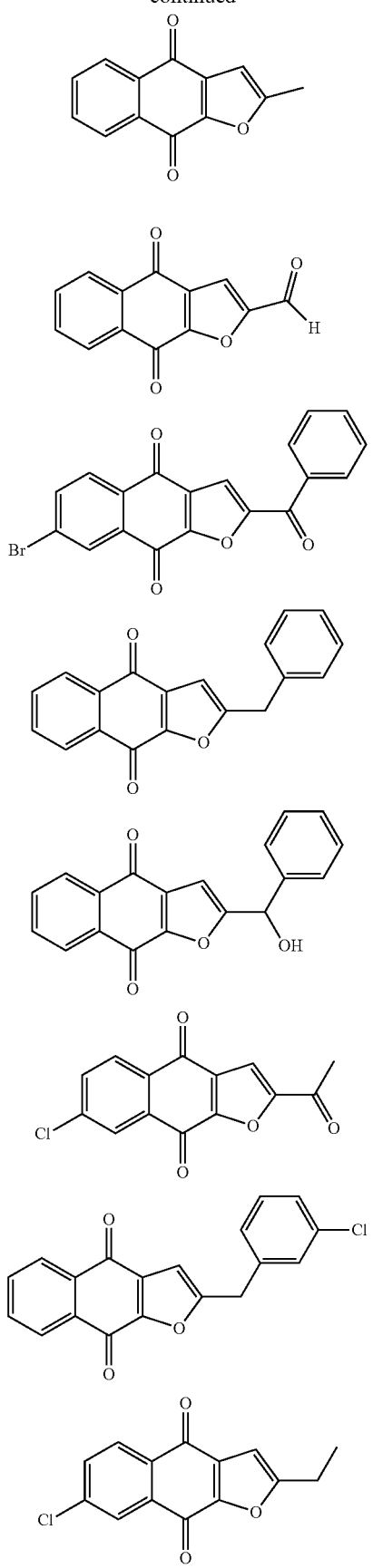

-continued

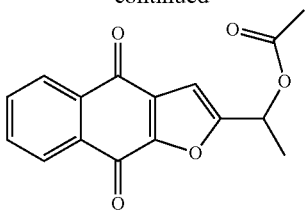

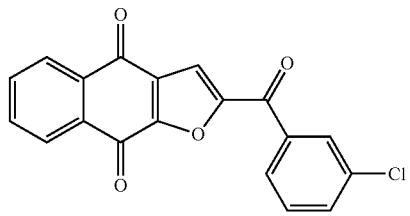

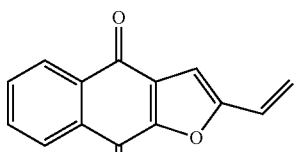

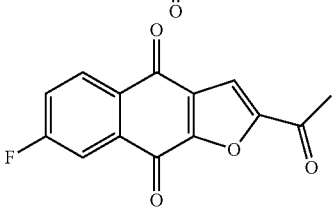

and

-continued

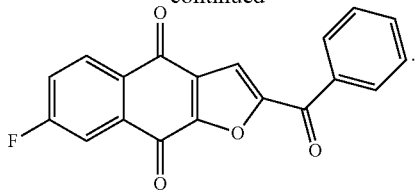

C. Uses

Stat3 pathway can be activated in response to cytokines, such as IL-6, or by a series of tyrosine kinases, such as EGFR, JAKs, Abl, KDR, c-Met, Src, and Her2. The downstream effectors of Stat3 include but not limited to Bcl-xl, c-Myc, cyclinD1, Vegf, MMP-2, and survivin. Stat3 pathway is found to be aberrantly active in a wide variety of human diseases, as shown in Table 1. Existing clinical samples examined showed that persistently active Stat3 pathway occurs in more than half of breast and lung cancers, hepatocellular carcinomas, multiple myelomas and more than 95% of head and neck cancers. Blocking Stat3 pathway causes cancer cell-growth arrest, apoptosis, and reduction of metastasis frequency in vitro and/or in vivo. Activated Stat3 has also been demonstrated in a number of autoimmune and inflammatory diseases. Furthermore, as interleukin-6 mediated inflammation is the common causative origin for Atherosclerosis [34], Peripheral Vascular Disease [35, 36], Coronary Artery Disease [35, 36], hypertension [37], Osteroprorosis [38], Type 2 Diabetes [35], and Dementia [39] and gp130-Jaks-Stats is the main pathway activated by IL-6, inhibition of the Stat3 pathway may treat or prevent these diseases as well. Therefore, Stat3 inhibitors are highly sought after therapeutic agents.

TABLE 1

Activation of STAT3 PATHWAY in human diseases

| | | DISEASES | | REF. |
|---|---|---|---|---|
| ONCOLOGY DISEASES | Solid Tumors | Breast Cancer | | [40] |
| | | Head and Neck Cancer (SCCHN) | | [41] |
| | | Lung Cancer | | [42] |
| | | Ovarian Cancer | | [43] |
| | | Pancreatic Cancer | | [44] |
| | | Colorectal carcinoma | | [45] |
| | | Prostate Cancer | | [46] |
| | | Renal Cell carcinoma | | [47] |
| | | Melanoma | | [48] |
| | | Hepatocellular carcinomas | | [12] |
| | | Cervical Cancer | | [49] |
| | | Endometrial Cancer | | [49] |
| | | Sarcomas | | [50, 51] |
| | | Brain Tumors | | [52] |
| | | Gastric Cancers | | [5] |
| | Hematologic Tumors | Multiple Myeloma | | [53] |
| | | Leukemia | HTLV-1-dependent Leukemia | [54] |
| | | | Chronic Myelogenous Leukemia | [47] |
| | | | Acute Myelogenous Leukemia | [55] |
| | | | Large Granular Lymphocyte Leukemia | [56] |
| | | Lymphomas | EBV-related/Burkitt's | [57] |
| | | | Mycosis Fungoides | [47] |
| | | | HSV Saimiri-dependent (T-cell) | [47] |
| | | | Cutaneous T-cell Lymphoma | [58] |
| | | | Hodgkin's Diseases | [47] |
| | | | Anaplastic Large-cell Lymphoma | [59] |

TABLE 1-continued

Activation of STAT3 PATHWAY in human diseases

| | | DISEASES | REF. |
|---|---|---|---|
| IMMUNE DISEASES | Inflammatory Diseases | Inflammatory Bowel Diseases | [60] |
| | | Inflammatory Arthritis | [61-63] |
| | | Crohn's Diseases | [64] |
| | | Chronic inflammatory conditions | [65] |
| | Autoimmune | Reumatoid Arthritis | [61, 62, 66-68] |
| | | Systemic lupus erythematosus | [69] |
| | Asthma | | [70] |
| | Allergy | | [71] |
| | Infections | | [72] |
| PROLIFERATIVE DISORDERS | Psoriasis | | [73] |
| | Keloids | | [74] |
| | Warts | | [75] |
| | Myelodysplastic syndrome | | [76] |
| | Polycythemia vera | | [77] |
| CNS DISEASES | Alzhemer's | | [78-80] |
| | Multiple sclerosis (MS) | | [78, 80, 81] |

The present invention provides, in part, Stat3 inhibitors, comprising of a compound of formula I-VIII of the present invention, or an enantiomer, diastereomer, tautomer, or pharmaceutically acceptable salt or solvate thereof.

The present invention further provides a method of treating a disorder related to aberrant Stat3 pathway activity in a mammal. The method of treating the disorder comprises administering to the mammal in need thereof an amount of a compound of formulae I through VIII, or an enantiomer, diastereomer, tautomer, or pharmaceutically acceptable salt or solvate thereof. The said aberrant Stat3 pathway activity can be identified by expression of phosphorylated Stat3 or its surrogate upstream or downstream regulators. In one embodiment, the condition is a cancer related to aberrant Stat3 pathway activity. In another embodiment, the condition is an autoimmune or inflammatory disease related to aberrant Stat3 pathway activity. The said autoimmune or inflammatory disease is selected from the group consisting of inflammatory bowel diseases, arthritis, Crohn's diseases, ulcerative colitis, rheumatoid arthritis, asthma, allergy, and systemic lupus erythematosus. In another embodiment, the condition is a CNS disease related to aberrant Stat3 pathway activity. The said CNS disease is selected from autoimmune demyelination disorder, Alzheimer's, stroke, ischemia reperfusion injury and multiple sclerosis. In yet another embodiment, the condition is a disease caused by inflammation and related to aberrant Stat3 pathway activity. These diseases include atherosclerosis, peripheral vascular disease, coronary artery disease, hypertension, osteroprorosis, type 2 diabetes, or dementia.

Recent studies have uncovered the presence of cancer stem cells with an exclusive ability to regenerate tumors. These cancer stem cells are functionally linked with continued malignant growth, cancer metastasis, recurrence, and cancer drug resistance. Cancer stem cells and their differentiated progeny appear to have markedly different biologic characteristics. They persist in tumors as a distinct, but rare population. Conventional cancer drug screenings depend on measurement of the amount of tumor mass and, therefore, are unlikely to identify drugs that act specifically on the stem cells. In fact, cancer stem cells have been demonstrated to be resistant to standard chemotherapies and are enriched after standard chemotherapy treatments, which result in cancer refractory and recurrence. Cancer stem cells have also been demonstrated to be resistant to radiotherapy [17]. The reported cancer types in which cancer stem cells have been isolated include breast cancer, head and neck cancer, lung cancer, ovarian cancer, pancreatic cancer, colorectal carcinoma, prostate cancer, melanoma, multiple myeloma, kaposi sarcoma, ewing's sarcoma, liver cancer, medulloblastoma, brain tumors, and leukemia. The mounting evidence linking cancer stem cells to tumorigenesis provides enormous therapeutic opportunity for targeting cancer stem cells. The key to unlocking this untapped potential is the identification and validation of pathways that are selectively important for cancer stem cell self-renewal and survival. Though multiple pathways underlying tumorigenesis in cancer and in embryonic stem cells or adult stem cells have been elucidated in the past, no pathways have been reported for cancer stem cell self-renewal and survival, largely due to the absence of a good system for doing so. We have identified that Stat3 is a key cancer stem cell survival and self-renewal factor. Therefore, Stat3 inhibitors can kill cancer stem cells and inhibit cancer stem cell self-renewal.

According to one or more embodiments of the present invention, cancer stem cell (CSC) or cancer stem cells (CSCs) refer to a minute population of cancer cells that have self-renewal capability and are tumorigenic. They are also called "Cancer Initiating Cells", "Tumor Initiating Cells", "Cancer Stem-Like Cells", "Stem-Like Cancer Cells", and "super malignant cells", etc. The methods of isolating these cells include but not limited to identification by their ability of efflux Hoechst 33342, identification by the surface markers these cells expressed, such as CD133, CD44, CD166, and others, and enrichment by their tumorigenic property.

The present invention provides, in part, a method of inhibiting/reducing/diminishing cancer stem cell survival and or self-renewal with an effective amount of a compound of formulae I through VIII, or an enantiomer, diastereomer, tautomer, or pharmaceutically acceptable salt or solvate thereof. These cancer stem cells can be identified by the surface markers, such as CD44, CD133, and CD166.

As cancer stem cells are resistant to conventional chemotherapies, the present invention provides, in part, a method of treating cancer refractory to conventional chemotherapies in a mammal, comprising to the mammal in need thereof a pharmaceutical composition comprising a compound of formulae I through VIII, or pharmaceutically acceptable salt or solvate thereof.

As cancer stem cells are the root of cancer and are fundamentally responsible for cancer recurrence, the present invention provides, in part, a method of treating recurrent cancer in a mammal that has failed surgery, chemo, or XRT, comprising administering to the mammal in need thereof a pharmaceutical composition comprising a compound of formulae I through VIII, or pharmaceutically acceptable salt or solvate thereof.

Similarly, as cancer stem cells are the seeds of cancer and are fundamentally responsible for cancer metastasis, the present invention provides, in part, a method of treating or preventing cancer metastasis in a mammal, comprising administering to the mammal in need thereof a pharmaceutical composition comprising a compound of formulae I through VIII, or pharmaceutically acceptable salt or solvate thereof.

The present invention further provides, in part, a method of treating cancer in a mammal, comprising administering to the mammal a therapeutically effective amount of a compound of formula I-VIII of the present invention, or an enantiomer, diastereomer, tautomer, or pharmaceutically acceptable salt or solvate thereof. In one embodiment, the said cancer above is selected from lung cancer, breast cancer, cervix cancer, colon cancer, liver cancer, pancreatic cancer, head and neck cancer, gastric cancer, and prostate cancer.

The present invention further provides, in part, a pharmaceutical composition comprising a compound of formulae I through VII, or an enantiomer, diastereomer, tautomer, or pharmaceutically acceptable salt or solvate thereof, and a pharmaceutically-acceptable excipient, carrier, or diluent.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the mammal being treated and the particular mode of administration. The amount of active ingredient, which can be combined with a carrier material to produce a single dosage form, will generally be that amount of the compound which produces a therapeutic effect. Generally, out of 100%, this amount will range, for example, from about 1% to about 99% of active ingredient, from about 5% to about 70%, from about 10% to about 30%.

Therapeutic compositions or formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the alcohol or inhibitor according to the invention is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, cetyl alcohol, glycerol monostearate, and polyethylene oxide-polypropylene oxide copolymer; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Additionally, cyclodextrins, e.g., hydroxypropyl-.beta.-cyclodextrin, may be used to solubilize compounds.

Besides inert diluents, the oral compositions can also include adjuvants such as wetting agents, emulsifying and suspending agents, sweetening, flavoring, coloring, perfuming and preservative agents. Suspensions, in addition to the alcohols or inhibitors according to the invention, may contain suspending agents as, for example, ethoxylated isostearyl alcohols, polyoxyethylene sorbitol and sorbitan esters, microcrystalline cellulose, aluminum metahydroxide, bentonite, agar—agar and tragacanth, and mixtures thereof.

Formulations of the pharmaceutical compositions of the invention for rectal or vaginal administration may be presented as a suppository, which may be prepared by mixing one or more alcohols or inhibitors according to the invention, with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active pharmaceutical agents of the invention. Formulations of the present invention which are suitable for vaginal administration also include pessaries, tampons, creams, gels, pastes, foams or spray formulations containing such carriers as are known in the art to be appropriate.

Dosage forms for the topical or transdermal administration of an alcohol or other inhibitor according to the invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an alcohol or other inhibitor according to the invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Ophthalmic formulations, eye ointments, powders, solutions and the like, are also contemplated as being within the scope of this invention.

Pharmaceutical compositions of this invention suitable for parenteral administration comprise one or more alcohols or inhibitors according to the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In some cases, in order to prolong the effect of the alcohol or inhibitor according to the invention, it is desirable to slow the absorption of the alcohol or inhibitor from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered composition is accomplished by dissolving or suspending the alcohol or inhibitor in an oil vehicle. One strategy for depot injections includes the use of polyethylene oxide-polypropylene oxide copolymers wherein the vehicle is fluid at room temperature and solidifies at body temperature.

The pharmaceutical compounds of this invention may be administered alone or in combination with other pharmaceutical agents, or with other anti-cancer therapies as described hereinabove, as well as in combination with a pharmaceutically-acceptable excipient, carrier, or diluent as described above.

D. Chemical Synthesis

The compounds of the present invention can be prepared using the methods described below, together with synthetic methods known one skilled in the art of organic synthesis, or variations thereon. The reactions are performed in solvents appropriate to the reagents and materials employed and are suitable for transformations being effected. The starting materials for the examples contained herein are either commercially available or are readily prepared by standard methods from known materials. For example, the following reactions are illustrations but not limitations of the preparation of some of the starting materials and examples used herein.

The process shown in Scheme 1 can be used for the preparation of compounds in Formula II, III and IV when $R_7$ is hydrogen and X is oxygen from starting material 1-1 which is commercially available when $R_1$ is hydrogen or can be readily made by one skilled in the art when $R_1$ is halogen. The reaction of 2-hydroxy-1,4-naphthoquinone 1-1 with the appropriate aldehydes gives 2-hydroxy-3-(1-Alkenyl)-1,4-naphthoquinone 1-2. Treatment of compound 1-2 with mercury acetate followed by hydrochloric acid affords 2-alkyl-naphtha[2,3-b]furan-4,9-dione 1-3. Oxidation of 1-3 with n-bromosuccinimide and lead tetraacetate gives 2-(1-acetoxy-alkyl)-4H,9H-naphtho[2,3-b]furan-4,9-dione 1-4. Hydrochloric acid treatment of compound 1-4 gives 2-(hydroxy-alkyl or arylmethyl)-4H,9H-naphtho[2,3-b]furan-4,9-dione 1-5 and 2-vinyl-4H,9H-naphtho [2,3-b]furan-4,9-dione 1-6.

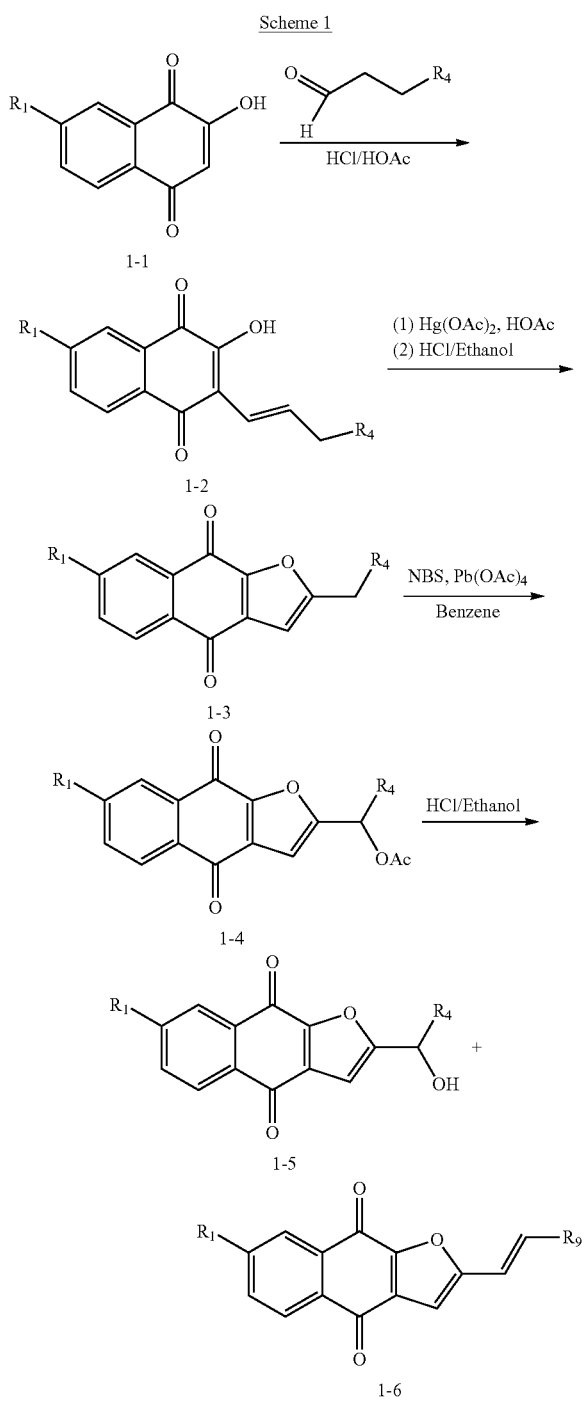

The process shown in Scheme 2 can be used for the preparation of compounds in Formula II, III and IV when $R_7$ is not hydrogen and X is oxygen from same starting material 1-1 as shown in Scheme 1. The reaction of 2-hydroxy-1,4-naphthoquinone 1-1 with the appropriate allylbromide gives 2-allyloxy-1,4-naphthoquinone 2-2. Rearrangement of 2-2 in ethanol afford 2-hydroxy-3-allyl-1,4-naphthoquinone 2-3, which can be cyclized by sulfuric acid treatment to form orthonaphthoquinone 2-4. Oxidation of 2-4 with n-bromosuccinimide and lead tetraacetate gives 3-acetoxy-orthonaphthoquinone 2-5. Hydrochloric acid treatment of compound 2-5 gives 2-alkyl (or aryl)-3-alkyl (or aryl)-naphtha[2,3-b]furan-4,9-dione 2-6.

The process shown in Scheme 3 can be used for the preparation of Formula I compounds when X is O by using 1-3 (or 2-6) as starting material. Oxidation of 2-alkyl (or benzyl)-7-alkyl (or aryl, hydrogen)-naphtha[2,3-b]furan-4,9-dione 1-3 (or 2-6) with chromium trioxide yields compound of formula 3-2.

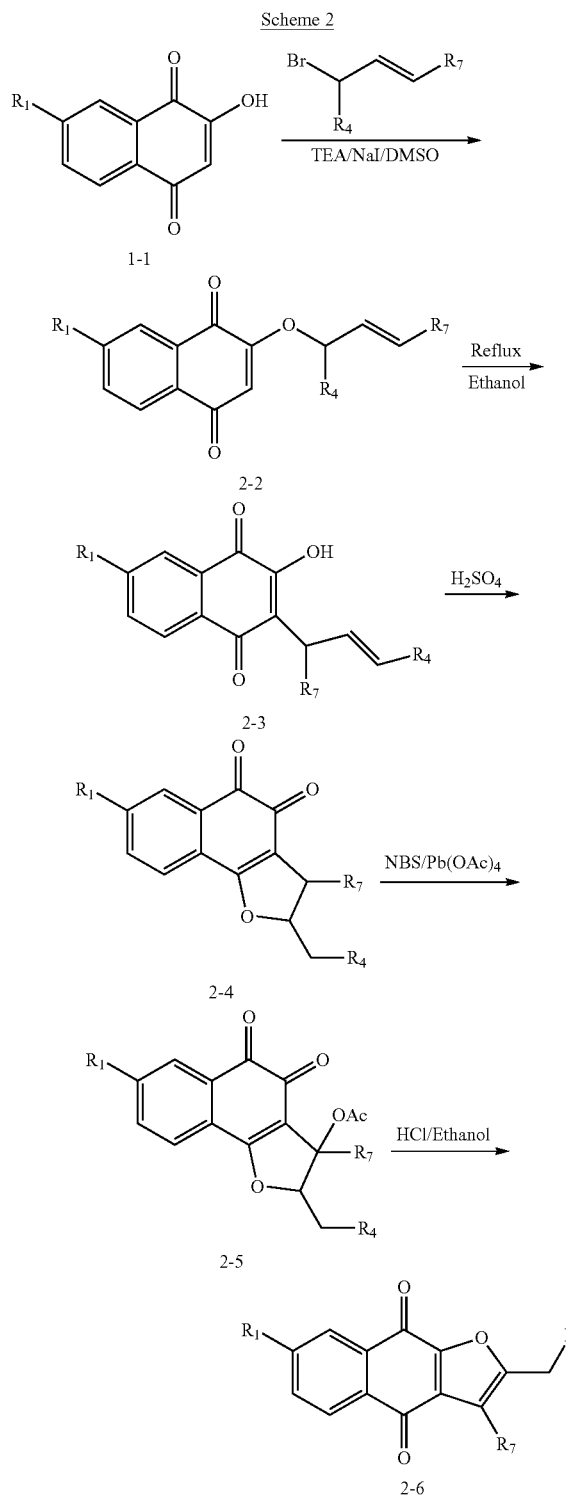

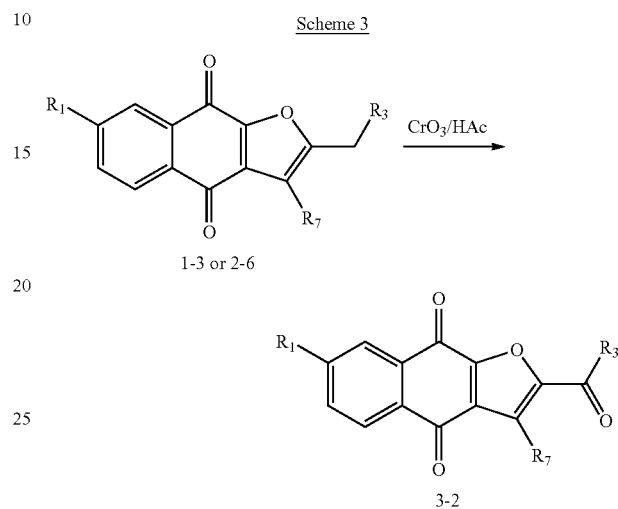

The process shown in Scheme 4 can be used for the preparation of Formula I, VI and VII compounds.

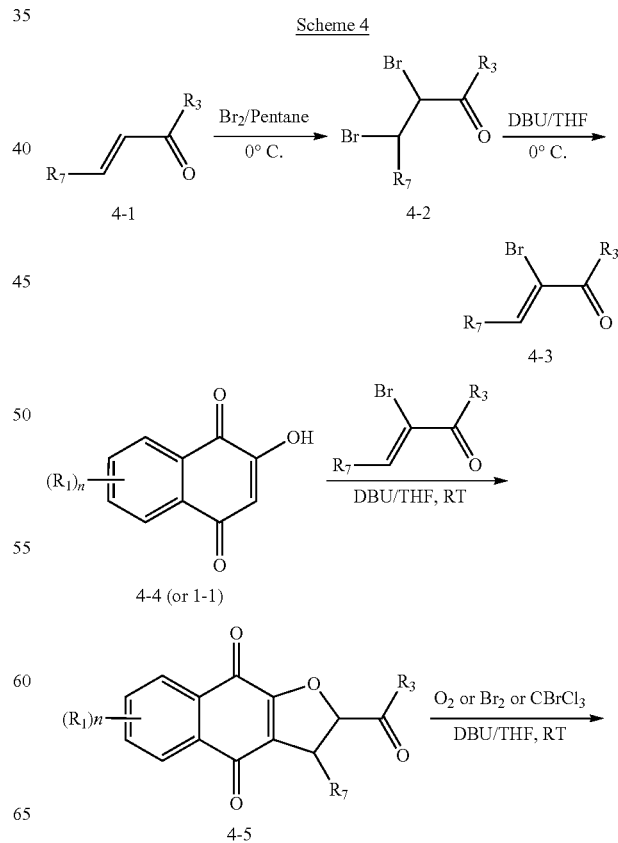

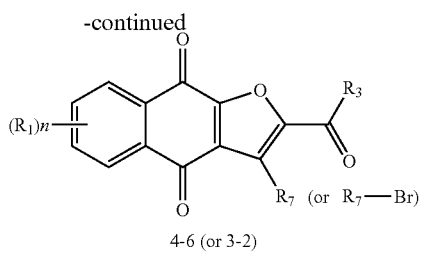

4-6 (or 3-2)

DBU: 1,8-Diazabicyclo[5.4.0]undec-7-ene;
THF: Tetrahydrofuran;
RT: room temperature.

The following non-limiting examples further illustrate the preparation of some of the starting materials and examples used herein.

Example 1

Preparation of sodium salt of 2-hydroxy-7-chloro-1,4-naphthoquinone 1-1 ($R_1$=Cl)

To the solution of 10 gram (0.06 mol) of 5-chloro-1-indanone in 200 ml of ethyl ether cooled in ice bath, 22 ml (0.066 mol) of 3 M methylmagnesium bromide in ethyl ether was dropped slowly over 30 min. The reaction mixture was stirred at room temperature overnight and then evaporated to dryness. 150 ml of 2 N hydrochloric acid in 50% ethanol was slowly dropped into the residue, and then refluxed for 1 hr. The mixture was extracted with dichloromethane and then the organic phase was washed with water and dried with sodium sulfate. The intermediate product 3-methyl-6-chloro-indene was purified by silica gel chromatograph.

To a vigorously stirred solution of 18 gram of sodium dichromate hydrate, 1 gram of sodium benzene sulfonate, and 50 ml of sulfuric acid in 250 ml of water, at 55° C., 7.5 gram (0.046 mol) of 3-methyl-6-chloro-indene was added dropwise in 1 hour. The mixture was then stirred for additional 20 minutes at 55° C. After chilling overnight at 0° C., the mixture was filtered, and the resulting solid was washed successively with cold water and benzene and dried under vacuum.

The crude intermediate product (5-chloro-2-acetyl)phenylacetic acid was dissolved in the mixture of 100 ml of anhydrous ethanol and 10 ml of sulfuric acid. Then the resulting mixture was stirred for 48 hours at room temperature. After diluting with 200 ml of water, the mixture was extracted with dichloromethane, and then the organic phase was washed with water and dried with sodium sulfate. The intermediate product ethyl (5-chloro-2-acetyl)phenylacetate was purified by silica gel chromatograph.

1.15 gram (0.050 mol) of sodium metal was suspended in 150 ml of anhydrous ethanol with vigorously stirring. After the sodium metal disappeared, 6 gram (0.025 mol) of ethyl (5-chloro-2-acetyl)phenylacetate was added, and the resulting mixture was stirred at room temperature in an open flask for 24 hours. The mixture was chilled to 0° C. and filtered, and the resulting brick red solid was washed with cold ethanol and dried under vacuum. 3.8 gram of sodium salt of 2-hydroxy-7-chloro-1,4-naphthoquinone 1-1 ($R_1$=Cl) was obtained: overall yield 27.5%. Mass (M-H) is 207.

Example 2

Preparation of sodium salt of 2-hydroxy-7-fluoro-1,4-naphthoquinone 1-1 ($R_1$=F)

Sodium salt of 2-hydroxy-7-fluoro-1,4-naphthoquinone 1-1 ($R_1$=F) was obtained from 10 gram (0.067 mol) of 5-fluoro-1-indanone by using the procedure described in example 1 to give brick red solid: 30% yield. Mass (M-H) is 191.

Example 3

Preparation of 2-hydroxy-3-(1-n-butenyl)-1,4-naphthoquinone 1-2 ($R_1$=H, $R_4$=CH$_3$)

To a solution of 20 gram (0.11 moles) of 2-hydroxy-1,4-naphthoquinone in 150 ml of DMSO and 20 ml of concentrated hydrochloride (37%) solution at 75° C., 20 ml of n-butyraldehyde (0.23 mol) was added. The mixture was vigorously stirred at the temperature of 72-78° C. for 4 hours, and then cooled by addition of 300 ml of ice water, and the resulting mixture was extracted with 300 ml of dichloromethane twice. The combined organic phases was washed successively with 500 ml of water, and 500 ml of 5% sodium bisulfite, and 500 ml of 4% sodium bicarbonate, and finally extracted with 400 ml of 5% sodium carbonate twice. The combined sodium carbonate extract was neutralized by addition of concentrated hydrochloric acid to pH 7.2-7.6. After chilling to 0° C., the mixture was filtered, and the resulting brick red solid was washed with cold water and dried under vacuum. 9.6 gram of product was obtained: 38.6% yield. $^1$H NMR (in CDCl$_3$) δ 1.12 (t, J=8, 3H), 2.31 (m, 2H), 6.60-6.65 (m, 1H), 7.07-7.15 (m, 1H), 7.66-7.77 (m, 3H), 8.06-8.15 (m, 2H).

Example 4

Preparation of 2-ethyl-4H,9H-naphtho[2,3-b]furan-4,9-dione 1-3 ($R_1$=H, $R_4$=CH$_3$)

A mixture of 9.6 gram (0.04 mol) of 2-hydroxy-3-(1-n-butenyl)-1,4-naphthoquinone 1-2 ($R_1$=H, $R_4$=CH$_3$) and 18.8 gram (0.094 mol) of mercury acetate in 300 ml of acetic acid was stirred at room temperature for 3 hours. The reaction mixture was filtered and then the filtrate was evaporated to dryness. The residue was suspended in 200 ml of concentrated hydrochloride (37%)/ethanol (1:2) and refluxed for 1 hour. After cooling down slowly to 0° C., the reaction mixture was filtered and the resulting solid product was washed with cooled 70% ethanol, and recrystallized in 70% ethanol to afford 5.1 gram of yellow crystals: 53.1% yield. 2-ethyl-4H,9H-naphtho[2,3-b]furan-4,9-dione 1-3 ($R_1$=H, $R_4$=CH$_3$), $^1$H NMR (in CDCl$_3$) δ 1.36 (t, J=8, 3H), 2.85 (q, J=7, 2H), 6.62 (s, 1H), 7.72-7.76 (m, 2H), 8.15-8.22 (m, 2H).

Example 5

Preparation of 2-methyl-4H,9H-naphtho[2,3-b]furan-4,9-dione 1-3 ($R_1$=H, $R_4$=H)

The intermediate product 2-hydroxy-3-(1-n-propenyl)-1,4-naphthoquinone 1-2 ($R_1$=H, $R_4$=H) was prepared according to the procedure described in example 3 by using 2-hydroxy-1,4-naphthoquinone 1-1 ($R_1$=H) and n-propionaldehyde as starting material. 2-methyl-4H,9H-naphtho[2,3-b]furan-4,9-dione 1-3 ($R_1$=H, $R_4$=H) was obtained from 10 gram (0.047 mol) of 1-2 ($R_1$=H, $R_4$=H) by using the procedure described in example 4 to afford yellow crystals; 50% yield. 2-methyl-4H,9H-naphtho[2,3-b]furan-4,9-dione 1-3 ($R_1$=H, $R_4$=H), $^1$H NMR (in CDCl$_3$) δ 2.52 (s, 3H), 6.61 (s, 1H), 7.70-7.77 (m, 2H), 8.14-8.22 (m, 2H);

Example 6

Preparation of 2-benzyl-4H,9H-naphtho[2,3-b]furan-4,9-dione 1-3 ($R_1$=H, $R_4$=C$_6$H$_5$)

The intermediate product 2-hydroxy-3-(3-phenyl-1-n-propenyl)-1,4-naphthoquinone 1-2 ($R_1$=H, $R_4$=C$_6$H$_5$) was prepared according to the procedure described in example 3 by using 2-hydroxy-1,4-naphthoquinone 1-1 ($R_1$=H) and hydrocinnamaldehyde as starting material. 2-benzyl-4H,9H-naphtho[2,3-b]furan-4,9-dione 1-3 ($R_1$=H, $R_4$=C$_6$H$_5$) was obtained from 10 gram (0.035 mol) of 1-2 ($R_1$=H, $R_4$=C$_6$H$_5$) by using the procedure described in example 4 to afford yellow crystals; 50% yield. 2-benzyl-4H,9H-naphtho[2,3-b]furan-4,9-dione 1-3 ($R_1$=H, $R_4$=C$_6$H$_5$), $^1$H NMR (in CDCl$_3$) δ 4.14 (s, 2H), 6.56 (s, 1H), 7.27-7.38 (m, 5H), 7.70-7.77 (m, 2H), 8.14-8.22 (m, 2H);

Example 7

Preparation of 2-ethyl-7-chloro-4H,9H-naphtho[2,3-b]furan-4,9-dione 1-3 ($R_1$=Cl, $R_4$=CH$_3$)

The intermediate product 2-hydroxy-3-(1-n-butenyl)-7-chloro-1,4-naphthoquinone 1-2 ($R_1$=Cl, $R_4$=CH$_3$) was prepared according to the procedure described in example 3 by using sodium salt of 2-hydroxy-7-chloro-1,4-naphthoquinone 1-1 ($R_1$=Cl) and n-butyraldehyde as starting material. 2-ethyl-7-chloro-4H,9H-naphtho[2,3-b]furan-4,9-dione 1-3 ($R_1$=Cl, $R_4$=CH$_3$) was obtained from 2 gram (0.0077 mol) of 1-2 ($R_1$=Cl, $R_4$=CH$_3$) by using the procedure described in example 4 to afford yellow crystals; 30% yield. 2-ethyl-7-chloro-4H,9H-naphtho[2,3-b]furan-4,9-dione 1-3 ($R_1$=Cl, $R_4$=CH$_3$) $^1$H NMR (in CDCl$_3$) δ 1.36 (t, J=8, 3H), 2.85 (q, J=7, 2H), 6.63 (s, 1H), 7.67 (d, J=8, 1H), 8.11 (d, J=8, 1H), 8.17 (s, 1H).

Example 8

Preparation of 2-ethyl-7-fluoro-4H,9H-naphtho[2,3-b]furan-4,9-dione 1-3 ($R_1$=F, $R_4$=CH$_3$)

The intermediate product 2-hydroxy-3-(1-n-butenyl)-7-fluoro-1,4-naphthoquinone 1-2 ($R_1$=F, $R_4$=CH$_3$) was prepared according to the procedure described in example 3 by using sodium salt of 2-hydroxy-7-fluoro-1,4-naphthoquinone 1-1 ($R_1$=F) and n-butyraldehyde as starting material. 2-ethyl-7-fluoro-4H,9H-naphtho[2,3-b]furan-4,9-dione 1-3 ($R_1$=F, $R_4$=CH$_3$) was obtained from 2 gram (0.0082 mol) of 1-2 ($R_1$=F, $R_4$=CH$_3$) by using the procedure described in example 4 to afford yellow crystals; 30% yield. 2-ethyl-7-fluoro-4H,9H-naphtho[2,3-b]furan-4,9-dione 1-3 ($R_1$=F, $R_4$=CH$_3$) $^1$H NMR (in CDCl$_3$) δ 1.36 (t, J=8, 3H), 2.86 (q, J=7, 2H), 6.63 (s, 1H), 7.35-7.40 (m, 1H), 7.85-7.88 (m, 1H), 8.18-8.22 (m, 1H).

Example 9

Preparation of 2-(1-acetoxyethyl)-4H,9H-naphtho[2,3-b]furan-4,9-dione 1-4 ($R_1$=H, $R_4$=CH$_3$)

To a solution of 4.53 gram (0.02 mol) of 2-ethyl-4H,9H-naphtho[2,3-b]furan-4,9-dione 1-3 ($R_1$=H, $R_4$=CH$_3$) in 200 ml of benzene, was added 7 g (0.04 mol) of N-bromosuccinimide and 7 g (0.016 mol) lead (IV) acetate. The mixture was refluxed for 24 hours, and then poured into 2 volume of 5% sodium bicarbonate solution. After filtration, the organic phase was separated and washed with water and dried with sodium sulfate and finally evaporated to dryness. The residue was purified by silica gel column chromatograph to yield pale yellow powder: 60% yield. 2-(1-acetoxyethyl)-4H,9H-naphtho[2,3-b]furan-4,9-dione 1-4 ($R_1$=H, $R_4$=CH$_3$) $^1$H NMR (in CDCl$_3$) δ 2.12 (d, J=7, 3H), 2.96 (s, 3H), 5.25 (q, J=7, 1H), 6.86 (s, 1H), 7.72-7.79 (m, 2H), 8.17-8.24 (m, 2H).

Example 10

Preparation of 2-(1-Hydroxyethyl)-4H,9H-naphtho[2,3-b]furan-4,9-dione 1-5 ($R_1$=H, $R_4$=CH$_3$) and 2-vinyl-4H,9H-naphtho[2,3-b]furan-4,9-dione 1-6 ($R_1$=H, $R_9$=H)

A mixture of 2.84 gram (0.01 mol) of 2-(1-acetoxyethyl)-4H,9H-naphtho[2,3-b]furan-4,9-dione 1-4 ($R_1$=H, $R_4$=CH$_3$) and 200 ml of 2N HCl in 70% ethanol was refluxed for 1 hour. After addition of 1 volume of ice water, the mixture was extracted with dichloromethane twice. The combined organic phase was washed with water and dried with sodium sulfate, and then evaporated to dryness. The residue was purified by silica gel column chromatograph to yield two pale yellow fractions. The late eluted fraction: 35% yield, 2-(1-hydroxyethyl)-4H,9H-naphtho[2,3-b]furan-4,9-dione 1-5 ($R_1$=H, $R_4$=CH$_3$) $^1$H NMR (in CDCl$_3$) δ 1.66 (d, J=7, 3H), 2.26 (broad s, 1H), 5.05 (q, J=7, 1H), 6.92 (s, 1H), 7.72-7.78 (m, 2H), 8.16-8.23 (m, 2H); The early eluted fraction: 43% yield, 2-vinyl-4H,9H-naphtho[2,3-b]furan-4,9-dione 1-6 ($R_1$=H, $R_9$=H) $^1$H NMR (in CDCl$_3$) δ 3.57 (q, J=7, 2H), 4.62 (q, J=7, 1H), 6.85 (s, 1H), 7.72-7.78 (m, 2H), 8.17-8.24 (m, 2H).

Example 11

Preparation of 2-(1-Hydroxyethyl)-7-fluoro-4H,9H-naphtho [2,3-b]furan-4,9-dione 1-5 ($R_1$=F, $R_4$=CH$_3$) and 2-vinyl-7-fluoro-4H,9H-naphtho[2,3-b]furan-4,9-dione 1-6 ($R_1$=F, $R_9$=H)

2-(1-acetoxyethyl)-4H,9H-naphtho [2,3-b]furan-4,9-dione 1-4 ($R_1$=F, $R_4$=CH$_3$) was prepared according to the procedure described in example 9 by using 2-ethyl-7-fluoro-4H,9H-naphtho[2,3-b]furan-4,9-dione 1-3 ($R_1$=F, $R_4$=CH$_3$) with yield of 55%. 2-(1-Hydroxyethyl)-7-fluoro-4H,9H-naphtho [2,3-b]furan-4,9-dione 1-5 ($R_1$=F, $R_4$=CH$_3$) and 2-vinyl-7-fluoro-4H,9H-naphtho[2,3-b]furan-4,9-dione 1-6 ($R_1$=F, $R_9$=H) were prepared according to the procedure described in example 10 with 35% yield for 1-5 ($R_1$=F, $R_4$=CH$_3$) $^1$H NMR (in CDCl$_3$) δ 1.66 (d, J=7, 3H), 2.20 (broad s, 1H), 5.05 (broad, 1H), 6.86 (s, 1H), 7.37-7.43 (m, 1H), 7.85-7.89 (m, 1H), 8.19-8.24 (m, 1H); and with 40% yield for 1-6 ($R_1$=F, $R_9$=H) $^1$H NMR (in CDCl$_3$) δ 3.58 (q, J=7, 2H), 4.61 (q, J=7, 1H), 6.86 (s, 1H), 7.37-7.42 (m, 1H), 7.88 (q, J=6, 1H), 8.22 (q, J=4, 1H).

Example 12

Preparation of 2-methyl-3-phenyl-4H,9H-naphtho[2,3-b]furan-4,9-dione 2-6 (R$_1$=H, R$_4$=H, R$_7$=C$_6$H)

To a solution of 20 gram (0.11 moles) of 2-hydroxy-1,4-naphthoquinone in 200 ml of DMSO, 16.5 grams (0.11 moles) of sodium iodide, 15.3 ml (0.11 moles) of triethylamine and 23.8 grams (0.12 moles) of cinnamyl bromide were added. The mixture was vigorously stirred at 50° C. overnight, and then cooled by addition of 400 ml of ice water, and the resulting mixture was extracted with 300 ml of toluene twice. The combined organic phase was washed successively with 500 ml of water, and 400 ml of 2N sodium hydroxide twice, and 500 ml of water. The organic phase was dried with sodium sulfate and evaporated to dryness. The crude product 2-2 (R$_1$=H, R$_4$=H, R$_7$=C$_6$H$_5$) residue was dissolved in 200 ml of anhydrous ethanol and refluxed for 3 hours. After evaporation, the residue was dissolved in 200 ml of toluene, and extracted with 200 ml of 2N sodium hydroxide twice. The combined extract was neutralized by addition of concentrated hydrochloric acid to pH 3-5, and extracted with 300 ml of dichloromethane. The dichloromethane solution was washed with equal volume of water, and dried with sodium sulfate, and then evaporated to yield crude lapachol analog 2-3 (R$_1$=H, R$_4$=H, R$_7$=C$_6$H$_5$). To 2 grams of crude 2-3 (R$_1$=H, R$_4$=H, R$_7$=C$_6$H$_5$), 20 ml of sulfuric acid was added, and the resulting mixture was placed at room temperature for 1 hour. The sulfuric acid mixture was poured into 200 ml of water and extracted with 200 ml of dichloromethane twice to give crude dunione analog 2-4 (R$_1$=H, R$_4$=H, R$_7$=C$_6$H$_5$) which was then purified with silica gel chromatograph. Treatment of 2-4 (R$_1$=H, R$_4$=H, R$_7$=C$_6$H$_5$) with N-bromosuccinimide and lead (IV) acetate was performed according to the procedure described in example 9 to give crude 2-5 (R$_1$=H, R$_4$=H, R$_7$=C$_6$H$_5$). Without silica gel chromatograph, the crude 2-5 (R$_1$=H, R$_4$=H, R$_7$=C$_6$H$_5$) was directly dissolved in 200 ml ethanol/concentrated HCl (1:1) and refluxed for 1 hour to give crude 2-6 (R$_1$=H, R$_4$=H, R$_7$=C$_6$H$_5$) which was purified with silica gel chromatograph. Overall yield 10%. 2-methyl-3-phenyl-4H,9H-naphtho[2,3-b]furan-4,9-dione 2-6 (R$_1$=H, R$_4$=H, R$_7$=C$_6$H$_5$) $^1$H NMR (in CDCl$_3$) δ 2.51 (s, 3H), 7.42-7.50 (m, 5H), 7.71-7.74 (m, 2H), 8.10-8.13 (m, 1H), 8.21-8.23 (m, 1H).

Example 13

Preparation of 2-Acetyl-4H,9H-naphtho[2,3-b]furan-4,9-dione 3-2 (R$_1$=H, R$_3$=CH$_3$, R$_7$=H)

To a solution of 5.52 gram (0.02 mol) of 2-ethyl-4H,9H-naphtho[2,3-b]furan-4,9-dione 1-3 (R$_1$=H, R$_4$=CH$_3$) in 100 ml of acetic acid and acetic anhydride (3:1), was added chromium (VI) oxide (6 g, 0.06 mol) in four portions at the interval of 30 minutes while stirred vigorously. After additional 48 hours at room temperature, the mixture was added one volume of water, and then chilled to 0° C. in ice bath and filtered. The resulting solid was washed with cold water, dried under vacuum, and recrystallized in ethyl acetate to give light yellow green crystal: 56% yield, 2-acetyl-4H,9H-naphtho[2,3-b]furan-4,9-dione 3-2 (R$_1$=H, R$_3$=CH$_3$, R$_7$=H) $^1$H NMR (in CDCl$_3$) δ 2.67 (s, 3H), 7.61 (s, 1H-3), 7.79-7.84 (m, 2H), 8.22-8.28 (m, 2H).

Example 14

Preparation of 2-benzoyl-4H,9H-naphtho[2,3-b]furan-4,9-dione 3-2 (R$_1$=H, R$_3$=C$_6$H$_5$, R$_7$=H)

To a solution of 5.76 gram (0.02 mol) of 2-benzyl-4H,9H-naphtho[2,3-b]furan-4,9-dione 1-3 (R$_1$=H, R$_4$=C$_6$H$_5$) in 100 ml of acetic acid and acetic anhydride (3:1), was added chromium (VI) oxide (6 g, 0.06 mol) in four portions at the interval of 30 minutes while stirred vigorously. After additional 48 hours at room temperature, the mixture was added two volume of water, and extracted with dichloromethane. The organic phase was washed with water and dried with sodium sulfate. After evaporation, the residue was subject to silica gel column chromatograph purification. The light yellow green powder was obtained, 45% yield, 2-benzoyl-4H,9H-naphtho[2,3-b]furan-4,9-dione 3-2 (R$_1$=H, R$_4$=C$_6$H$_5$, R$_7$=H) $^1$H NMR (in CDCl$_3$) δ 7.56-7.60 (m, 2H), 7.66-7.70 (m, 1H), 7.71 (s, 1H-3), 7.80-7.84 (m, 2H), 8.10-8.13 (m, 2H), 8.24-8.30 (m, 2H).

Example 15

Preparation of 2-benzoyl-7-bromo-4H,9H-naphtho[2,3-b]furan-4,9-dione 3-2 (R$_1$=Br, R$_4$=C$_6$H$_5$, R$_7$=H)

The intermediate 1-1 (R$_1$=Br) was prepared by using 5-bromo-1-indanone as starting material according to the procedure described in Example 1.

The intermediate 1-2 (R$_1$=Br, R$_4$=C$_6$H$_5$) was prepared according to the procedure described in Example 3 by using 1-1 (R$_1$=Br) and hydrocinnamaldehyde as starting materials.

The intermediate 1-3 (R$_1$=Br, R$_4$=C$_6$H$_5$) was prepared according to the procedure described in Example 6 by using 1-2 (R$_1$=Br, R$_4$=C$_6$H$_5$) as starting material.

The 2-benzoyl-7-bromo-4H,9H-naphtho[2,3-b]furan-4,9-dione 3-2 (R$_1$=Br, R$_3$=C$_6$H$_5$, R$_7$=H) was obtained according to the procedure described in Example 14 by using 1-3 (R$_1$=Br, R$_4$=C$_6$H$_5$) as starting materials with yield of 25%, $^1$H NMR (in CDCl$_3$) δ 7.58 (t, J=8, 2H), 7.67-7.72 (m, 2H), 7.93-7.96 (m, 1H), 8.09-8.12 (m, 3H), 8.4 (d, J=2, 1H).

Example 16

Preparation of 2-Acetyl-7-chloro-4H,9H-naphtho[2,3-b]furan-4,9-dione 3-2 (R$_1$=Cl, R$_3$=CH$_3$, R$_7$=H)

The 2-acetyl-7-chloro-4H,9H-naphtho [2,3-b]furan-4,9-dione 3-2 (R$_1$=Cl, R$_3$=CH$_3$, R$_7$=H) was obtained according to the procedure described in example 13 by using 2-ethyl-7-chloro-4H,9H-naphtho [2,3-b]furan-4,9-dione 1-3 (R$_1$=Cl, R$_4$=CH$_3$) as starting materials with yield of 30%. $^1$H NMR (in CDCl$_3$) δ 2.67 (s, 3H), 7.61 (s, 1H), 7.74-7.78 (m, 1H), 8.17-8.23 (m, 2H).

Example 17

Preparation of 2-Acetyl-7-fluoro-4H,9H-naphtho[2,3-b]furan-4,9-dione 3-2 (R$_1$=F, R$_3$=CH$_3$, R$_7$=H)

The 2-acetyl-7-fluoro-4H,9H-naphtho[2,3-b]furan-4,9-dione 3-2 (R$_1$=F, R$_3$=CH$_3$, R$_7$=H) was obtained according to the procedure described in example 13 by using 2-ethyl-7-fluoro-4H,9H-naphtho[2,3-b]furan-4,9-dione 1-3 (R$_1$=F, R$_4$=CH$_3$) as starting materials with yield of 30%, $^1$H NMR (in CDCl$_3$) δ 2.67 (s, 3H), 7.44-7.49 (m, 1H), 7.61 (s, 1H), 7.90-7.93 (m, 1H), 8.25-8.30 (m, 1H).

Example 18

Preparation of 2-Acetyl-3-bromomethyl-4H,9H-naphtho[2,3-b]furan-4,9-dione 4-6(R$_1$=H, R$_3$=—CH$_3$, and R$_7$=—CH$_2$Br)

To a solution of 5 gram (0.0594 moles) of 3-penten-2-one in 100 ml of pentane in ice bath with vigorously stirring, was slowly added 9.5 grams (0.0594 moles) of bromine in 20 ml of pentane within 30 minutes. After stirred for additional 5 minutes in ice bath, the mixture was evaporated to remove most of pentane. The small volume of 3,4-dibromo-2-pentanone residue from step 1 was dissolved in 200 ml of THF, and then chilled in an ice bath. To the solution in ice bath with vigorously stirring, was slowly added 9.0 grams (0.0594 moles) of DBU within 30 minutes. Large quantity of precipitate salt was generated. The mixture was directly used for next step reaction. To the reaction mixture of 3-bromo-3-penten-2-one, 10.4 grams (0.0594 moles) of 2-hydroxy-1,4-naphthoquinone was added. The resulting mixture was stirred vigorously in a room temperature water bath. Then 9.9 grams (0.0650 moles) of DBU in was slowly added to the mixture within 30 minutes. The temperature of the reaction mixture rose by the heat generated from reaction and was controlled to below 35° C. by adding ice to the water bath. After vigorously stirred for additional 3 hours under air at room temperature, the mixture was evaporated to small volume, then 500 ml of water was added to the residue. The resulting mixture was extracted with dichloromethane. The organic phase was washed with water, aqueous 5% sodium bicarbonate and water, respectively, and then dried with sodium sulfate. 200 mg of 2-Acetyl-3-methyl-4H,9H-naphtho[2,3-b]dihydrofuran-4,9-dione was obtained by silica gel purification. 2-Acetyl-3-methyl-4H,9H-naphtho[2,3-b]dihydrofuran-4,9-dione 4-5 (R$_1$=H, R$_3$=R$_7$=CH$_3$) $^1$H NMR (in CDCl$_3$) δ 1.55d, J=7, 3H), 2.35 (s, 3H), 3.58 (m, 1H), 4.75 (d, J=7, 1H), 7.69-7.77 (m, 2H), 8.06-8.12 (m, 2H). The purified dihydrofuran intermediate was dissolved in dichloromethane. To the solution, 300 mg of bromine was added and the resulting mixture was stirred at room temperature overnight. The mixture was evaporated to small volume and loaded onto silica gel column. The desired pure 2-acetyl-3-bromomethyl-4H,9H-naphtho[2,3-b]furan-4,9-dione 4-6 (R$_1$=H, R$_3$=CH$_3$, R$_7$=BrCH$_2$) was obtained. $^1$H NMR (in CDCl$_3$) δ 2.78 s, 3H), 4.51 (s, 2H), 7.80-7.83 (m, 2H), 8.21-8.27 (m, 2H).

Example 19

Biological Assays

Compounds of the present invention can be tested according to the protocol described above. Table 2 shows the list of compounds described in the protocol.

TABLE 2

| Structure | Compound |
|---|---|
| 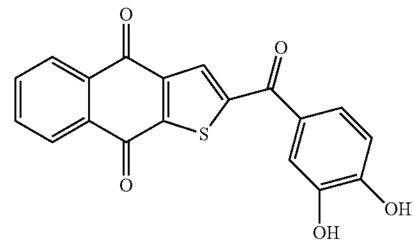 [SMILES: O=C(c1ccc(O)c(O)c1)c1cc2c(s1)C(=O)c1ccccc1C2=O] | 411 |
| 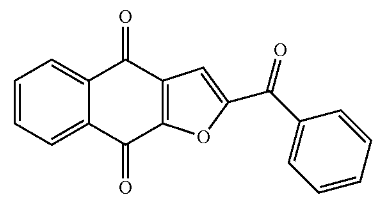 [SMILES: O=C(c1ccccc1)c1cc2c(o1)C(=O)c1ccccc1C2=O] | 412 |
| 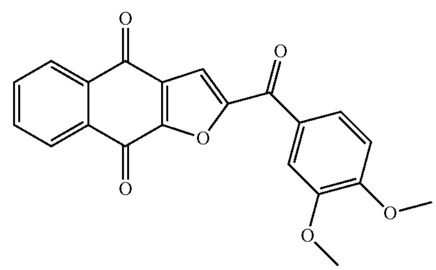 [SMILES: COc1ccc(C(=O)c2cc3c(o2)C(=O)c2ccccc2C3=O)cc1OC] | 413 |
| 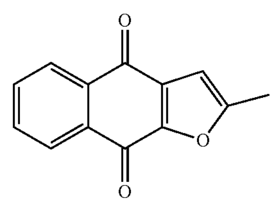 [SMILES: Cc1cc2c(o1)C(=O)c1ccccc1C2=O] | 102 |
| 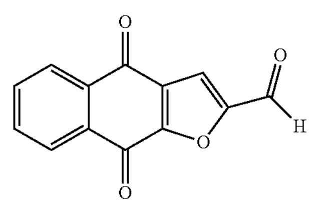 [SMILES: O=Cc1cc2c(o1)C(=O)c1ccccc1C2=O] | 414 |
| 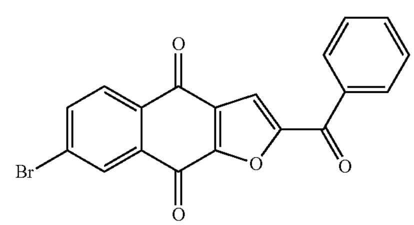 [SMILES: O=C(c1ccccc1)c1cc2c(o1)C(=O)c1cc(Br)ccc1C2=O] | 415 |
| 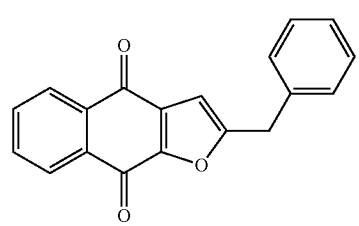 [SMILES: O=C1c2ccccc2C(=O)c2oc(Cc3ccccc3)cc21] | 103 |

TABLE 2-continued

| Structure | Compound |
|---|---|
| 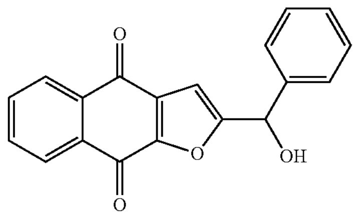 [SMILES: O=C1c2ccccc2C(=O)c2oc(C(O)c3ccccc3)cc21] | 302 |
| 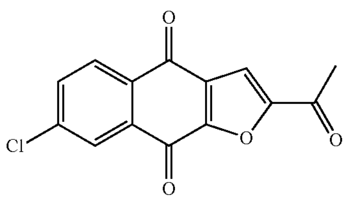 [SMILES: CC(=O)c1cc2c(o1)C(=O)c1cc(Cl)ccc1C2=O] | 416 |
| 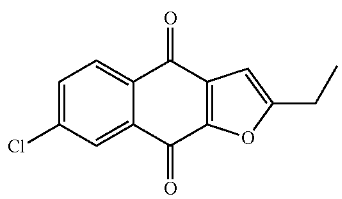 [SMILES: CCc1cc2c(o1)C(=O)c1cc(Cl)ccc1C2=O] | 105 |
| 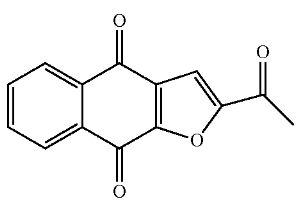 [SMILES: CC(=O)c1cc2c(o1)C(=O)c1ccccc1C2=O] | 401 |
| 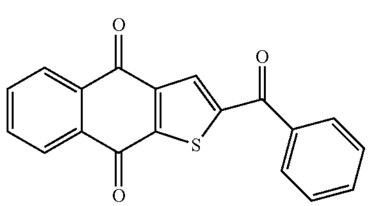 [SMILES: O=C(c1ccccc1)c1cc2c(s1)C(=O)c1ccccc1C2=O] | 402 |
| 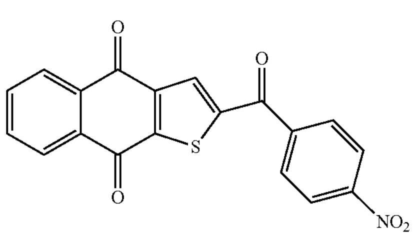 [SMILES: O=C(c1ccc([N+](=O)[O-])cc1)c1cc2c(s1)C(=O)c1ccccc1C2=O] | 403 |
| 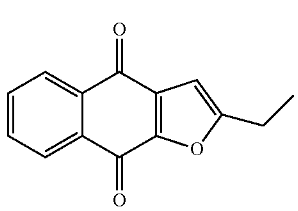 [SMILES: CCc1cc2c(o1)C(=O)c1ccccc1C2=O] | 101 |

TABLE 2-continued

| Structure | Compound |
|---|---|
| 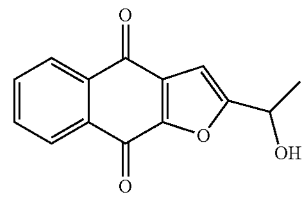 [SMILES: CC(O)c1cc2c(o1)C(=O)c1ccccc1C2=O] | 301 |
| 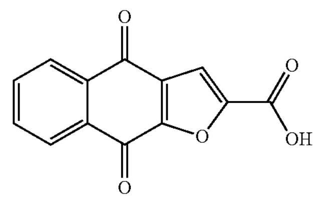 [SMILES: O=C(O)c1cc2c(o1)C(=O)c1ccccc1C2=O] | 405 |
| 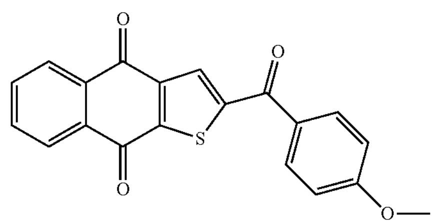 [SMILES: COc1ccc(C(=O)c2cc3c(s2)C(=O)c2ccccc2C3=O)cc1] | 407 |
| 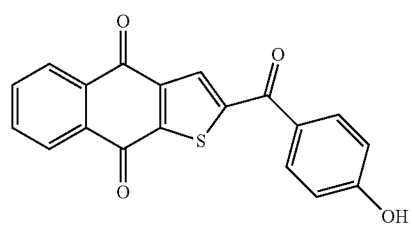 [SMILES: O=C(c1ccc(O)cc1)c1cc2c(s1)C(=O)c1ccccc1C2=O] | 408 |
| 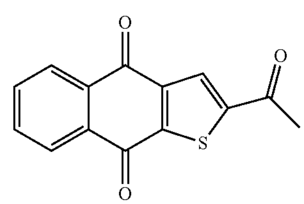 [SMILES: CC(=O)c1cc2c(s1)C(=O)c1ccccc1C2=O] | 409 |
| 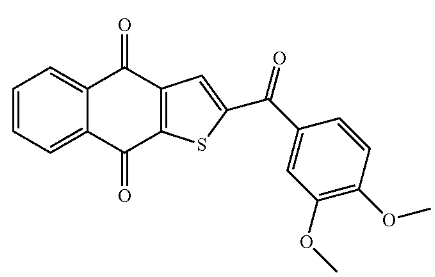 [SMILES: COc1ccc(C(=O)c2cc3c(s2)C(=O)c2ccccc2C3=O)cc1OC] | 410 |
| 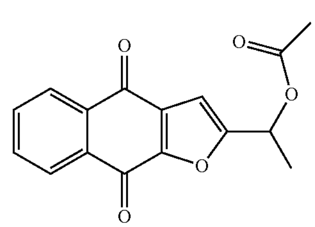 [SMILES: CC(=O)OC(C)c1cc2c(o1)C(=O)c1ccccc1C2=O] | 303 |

TABLE 2-continued

| Structure | Compound |
|---|---|
| 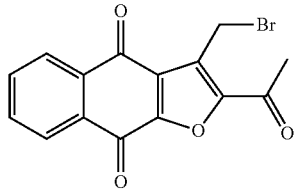 [SMILES: CC(=O)c1oc2c(c1CBr)C(=O)c1ccccc1C2=O] | 420 |
| 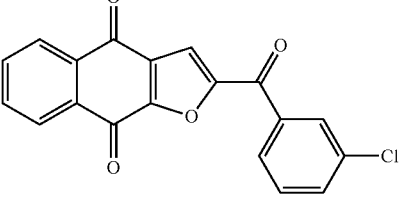 | 417 |
| 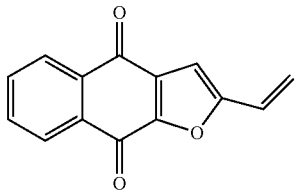 [SMILES: C=Cc1cc2c(o1)C(=O)c1ccccc1C2=O] | 201 |
| 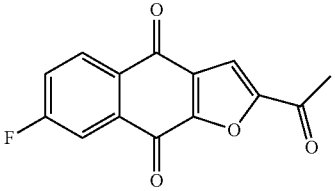 [SMILES: CC(=O)c1cc2c(o1)C(=O)c1cc(F)ccc1C2=O] | 418 |
| 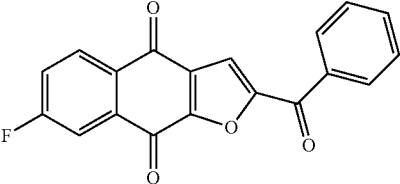 [SMILES: O=C(c1ccccc1)c1cc2c(o1)C(=O)c1cc(F)ccc1C2=O] | 419 |
| 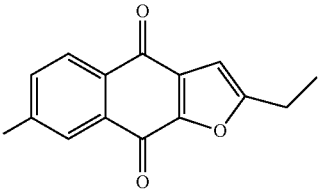 | 106 |
| 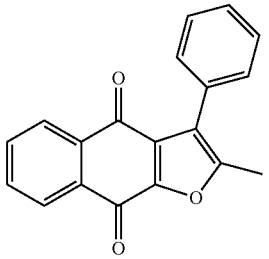 [SMILES: Cc1oc2c(c1-c1ccccc1)C(=O)c1ccccc1C2=O] | 108 |

TABLE 2-continued

| Structure | Compound |
|---|---|
| 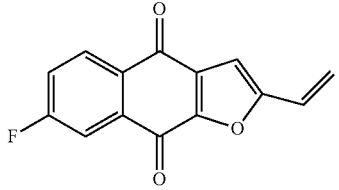 | 202 |
| 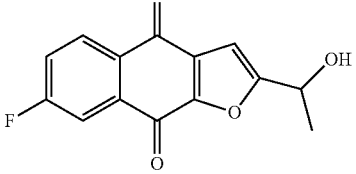 | 304 |
| 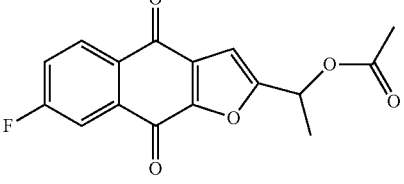 | 305 |
| 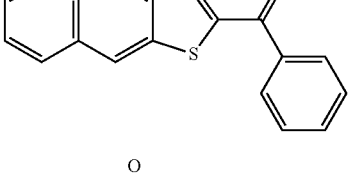 | 1001 |
| 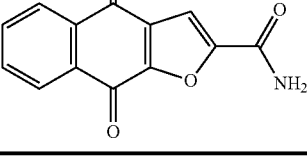 | 404 |

Cell Culture:

HeLa, DU145, H1299, DLD1, SW480, A549, MCF7, LN18, HCT116, HepG2, Paca2, Panc1, LNcap, FaDu, HT29, and PC3 cells (ATCC, Manassas, Va.) were maintained in Dulbecco's Modified Eagle Medium (DMEM) (Invitrogen, Carlsbad, Calif.) supplemented with 10% fetal bovine serum (FBS) (Gemini Bio-Products, West Sacramento, Calif.) and 5% penicillin/streptomycin/amphotercin B (Invitrogen).

Luciferase Reporter Assay:

HeLa Cells were co-transfected with Stat3-luciferase (Stat3-Luc) reporter vector (Panomics, Fremont, Calif.) and *Renilla luciferase* (Promega, Madison, Wis.) using Lipofectamine 2000 as described by the manufacturer (Invitrogen). Following transfection, cells were maintained in medium containing 0.5% FBS for 24 hours. Cells were then treated with the indicated compound for 30 minutes prior to the addition of 25 ng/ml oncostatin M (OSM) (R&D Systems, Minneapolis, Minn.) to the medium. 6 hours following OSM addition, cells were harvested and levels of firefly and renilla luciferase were measured using the Dual-Glo Luciferase Assay System as described by the manufacturer (Promega).

STAT3 DNA Binding Assay:

Electrophoretic mobility shift assay (EMSA) was performed as described by the manufacturer (Li-Cor Biosciences, Lincoln, Nebr.). Briefly, nuclear extracts were made from HeLa cells using the NucBuster Protein Extraction Kit as described by the manufacturer (EMD Biosciences, San Diego, Calif.). 5 μg of nuclear extract was pre-incubated with the indicated dose of indicated compound for 30 minutes prior to a 15-minute incubation with the IR700-labeled consensus Stat3 oligonucleotide. Samples were then electrophoresed on a polyacrylamide gel and directly scanned using the Odyssey infrared imaging system (Li-Cor Biosciences). For the enzyme-linked immunosorbent assay (ELISA), 5 μg of nuclear extract was preincubated with indicated concentration of indicated compound for 30 minutes prior to the addition of biotinylated oligo (5'-Biotin-GATCCTTCTGGGAATTCCTAGATC-3'). Stat3-DNA complexes were then captured on streptavidin coated 96 well plates (Pierce, Rockford, Ill.). Bound complexes were then incubated with Stat3 polyclonal antibody (Santa Cruz Biotechnology, Santa Cruz, Calif.) followed by anti-rabbit HRP conjugated secondary antibody (GE Healthcare, Pittsburgh, Pa.). Bound antibody was then visualized by addition of TMB substrate (Pierce) and absorbance measured at 450 nm.

Cell Viability Determination:

For 3-(4,5 dimethylthiazol-2-yl)-2,5-diphenyltetrazolium (MTT) (Sigma-Aldrich, St. Louis, Mo.) analysis, cells were plated in 96 well plates at 10,000 cells per well. 24 hours after plating, compound was added to cells at indicated doses. 22 hours following compound addition, MTT was added to each well (0.5 mg/ml, final concentration) and plates were incubated for an additional 2 hours at 37° C. Medium was then aspirated and the formazan product was solubilized in 100 μl of isopropyl alcohol. The absorbance of each well was measured at 570 nm using a microplate reader.

Hoechst Side Population:

To identify and isolate side population (SP) and non-SP fractions, SW480 cells were removed from the culture dish with trypsin and EDTA, pelleted by centrifugation, washed with phosphate-buffered saline (PBS), and resuspended at 37° C. in Dulbecco's modified Eagle's medium (DMEM) containing 2% FBS and 1 mM HEPES. The cells were then labeled with Hoechst 33342 (Invitrogen) at a concentration of 5 μg/mL. The labeled cells were incubated for 120 minutes at 37° C., either alone or with 50 μM verapamil (Sigma-Aldrich, St. Louis). After staining, the cells were suspended in Hanks' balanced saline solution (HBSS; Invitrogen) containing 2% FBS and 1 mM HEPES, passed a through 40 μm mesh filter, and maintained at 4° C. until flow cytometry analysis. The Hoechst dye was excited at 350 nm, and its fluorescence was measured at two wavelengths using a 450 DF10 (450/20 nm band-pass filter) and a 675LP (675 nm long-pass edge filter) optical filter. The gating on forward and side scatter was not stringent, and only debris was excluded [26].

CSC Isolation with Surface Markers:

Sorting tumor cells based primarily upon the differential expression of the surface marker(s), such as CD44 or CD133, have accounted for the majority of the highly tumorigenic CSCs described to date. CD133 isolation is based upon the method of Ricci-Vitiani et al. [31], with slight modification. CD133$^+$ cells were isolated by either fluorescence activated cell sorting (FACS) or magnetic nanoparticle-based separation. Briefly, $10^7$ cells/mL were labeled with CD133/1 (AC133)-PE for FACS-based cell sorting; or with CD133/1 (AC133)-biotin (Miltenyi Biotec, Auburn, Calif.) for magnetic field-based separation using the EasySep® biotin selection kit (Miltenyi Biotec) according to the manufacturer's recommendations. Non-specific labeling was blocked with the supplied FcR blocking reagent and antibody incubations (1:11) were carried out on ice for 15 minutes in PBS with 2% FBS and 1 mM EDTA. Five washes were done for EasySep® isolation, whereas cells were pelleted at 400×g for 5 minutes and resuspended at $2 \times 10^7$/mL, before sorting by FACS.

CD44$^{high}$ cells were isolated by FACS according to the methods described in Ponti et al, with slight modification [82]. Briefly, after trypsinization and recovery of cells for 30 minutes at 37° C. in growth media, cells were pelleted at 400×g and were resuspended in PBS with 2% FBS and 1 mM EDTA at $1 \times 10^6$ cells/mL. Cells were then incubated on ice with a 1:100 dilution of CD44-FITC (BD Biosicences, San Diego, Calif.) for 15 minutes. Alternatively, CD24-PE (BD Biosicences, San Diego, Calif.) (1:100) was utilized for negative selection. After washing three times, cells were resuspended at $2 \times 10^6$/mL and passed through a 40 μM mesh before sorting Sphere Assay:

A reliable method of measuring the self-renewal capacity of cell population if the ability to be cultured as spheres in the absence of serum or attachment. CD44$^{high}$ FaDu or Hoechst side population cancer stem cells were cultured in ultra low attachment plates in cancer stem cell media (DMEM/F12, B27 Neurobasal supplement, 20 ng/ml EGF, 10 ng/ml FGF, 4 μg/ml insulin, and 0.4% BSA) to allow spheres formation. Typically, sphere formation was evaluated by microscopy after 10-14 days in culture and spheres with >50 cells were scored.

Example 20

Identification of Compounds that Selectively Kill a Broad Spectrum of Cancer Cells Identification of Compounds that are Apoptotic to a Broad Spectrum of Cancer Cells In Vitro.

Cells plated in 96 well plates and treated with indicated compounds were subjected to MTT analysis at 24 hours following compound treatment to determine cell viability. IC$_{50}$ values calculated across multiple cell lines are summarized in Table 3 and Table 4 below. The data demonstrate that these compounds have potent activity against broad spectrum of cancer cells.

TABLE 3

| Cell Line | Tissue | IC$_{50}$ (μM) | | | | |
|---|---|---|---|---|---|---|
| | | #401 | #402 | #412 | #416 | #418 |
| A549 | Lung | 0.95 | | 3.16 | 1.90 | 1.06 |
| H1299 | Lung | 0.23 | 1.04 | 0.52 | 0.25 | 0.34 |
| MCF7 | Breast | 0.46 | | 1.15 | 0.75 | 0.46 |
| HeLa | Cervix | 0.43 | 2.01 | 1.69 | 0.62 | 0.80 |
| DLD1 | Colon | 0.33 | 2.51 | 1.11 | 0.54 | 0.64 |
| SW480 | Colon | 0.32 | 1.49 | 1.31 | 0.44 | 0.76 |
| HCT116 | Colon | 0.58 | | 2.02 | 0.69 | 0.61 |
| HT29 | Colon | 1.27 | | 4.64 | 1.91 | 1.83 |
| HepG2 | Liver | 0.25 | | | | |
| Paca2 | Pancreas | 0.11 | 0.49 | 0.64 | 0.21 | 0.21 |
| Panc1 | Pancreas | 1.70 | 7.21 | 3.69 | 2.59 | 1.54 |
| DU145 | Prostate | 0.12 | 0.55 | 0.33 | 0.22 | 0.18 |
| PC3 | Prostate | 2.37 | 8.48 | 4.45 | 3.10 | 3.04 |
| LNCap | Prostate | 0.63 | | | | |
| FaDu | Head and Neck | 0.39 | | | | |

TABLE 4

| Compound # | IC$_{50}$ (μM) DU145 | IC$_{50}$ (μM) H1299 | IC$_{50}$ (μM) Hela | IC$_{50}$ (μM) FaDu |
|---|---|---|---|---|
| 401 | 0.116 | 0.234 | 0.428 | 0.39 |
| 402 | 0.554 | 1.039 | 2.013 | |
| 403 | 6.5 | 4 | | |
| 101 | 3.7 | 3-10 | 11.7 | |
| 301 | 0.835 | 0.794 | 3.358 | |
| 405 | 1.405 | | | |
| 407 | 2.105 | 4.113 | 3.779 | |
| 408 | 0.554 | 3.617 | 4.471 | |
| 409 | 0.442 | 1.033 | 1.880 | |
| 410 | 0.239 | 1.876 | 2.515 | |
| 411 | 0.616 | 14.052 | 14.748 | |
| 412 | 0.327 | 0.524 | 1.689 | |
| 413 | 0.721 | 1.897 | 4.375 | |
| 102 | | | 11.418 | |
| 414 | 14.092 | 11.315 | 13.031 | |
| 415 | 9.8 | 6.5 | 10.5 | |
| 103 | >10 | 8.9 | 16.7 | |
| 302 | 4.9 | 7.2 | 7.8 | |
| 416 | 0.211 | 0.337 | 0.711 | |
| 105 | 6.5 | 8.4 | 13 | |
| 303 | 2.881 | | | |
| 417 | 0.768 | | | |
| 201 | 1.756 | | | |
| 418 | 0.164 | 0.317 | 0.488 | |
| 419 | 1.822 | | | |
| 106 | 4.84 | | | |
| 108 | 30.848 | | 20.713 | |
| 202 | 2.645 | | 4.558 | |
| 304 | 1.841 | | 1.67 | |
| 305 | 1.104 | | 1.707 | |
| 420 | | | | 3.5 |

Example 21

Identification of Stat3 as an Anti-Cancer Stem Cell Target

Figure 3A:
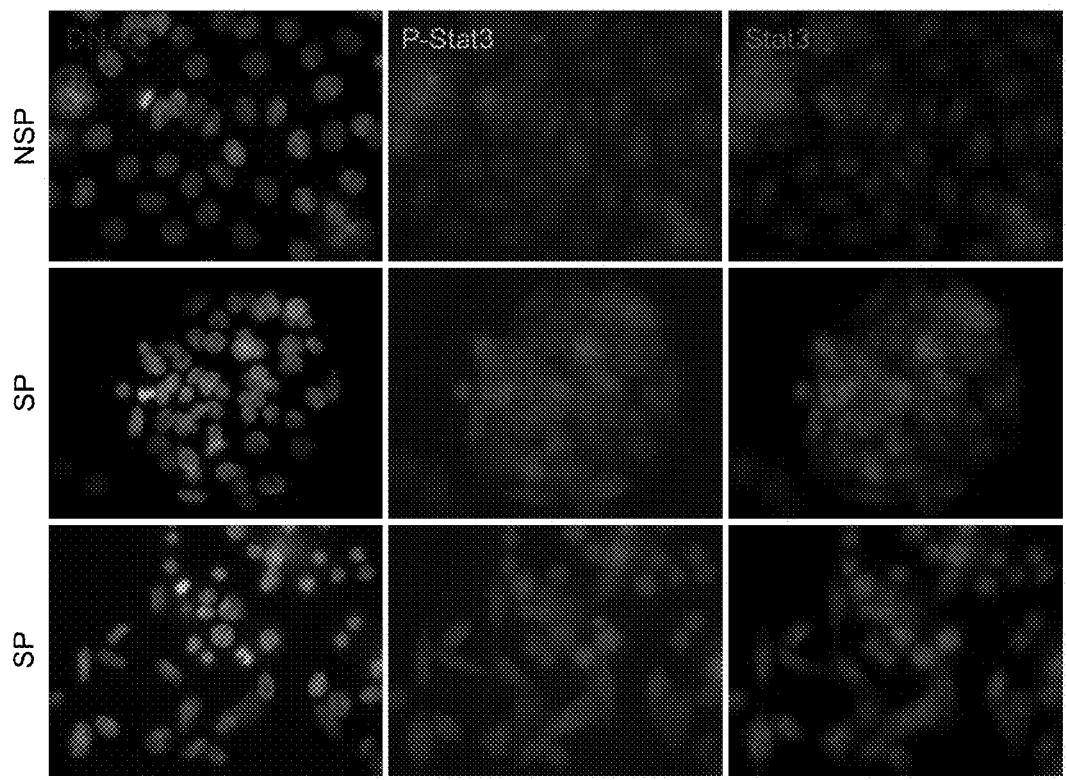
FIG. 3A shows that Stat3 is constitutively active in Hoechst Side Population cells.

Stat3 knockdown in CSCs induces apoptosis. To determine whether cancer stem cells expressed Stat3 and whether Stat3 was constitutively active, we performed immunofluorence microscopy, which allows not only the analysis of rare cell populations, but also provides additional information on protein localization and the ability to correlate staining with phenotype (i.e. apoptosis). Following immunofluorescent detection of p-Stat3 and Stat3 in NSP and SP cells isolated by FACS from SW480 colon cancer cells, we determined that Stat3 was indeed present in SP cells and that it was modestly enriched in the nucleus (FIG. 3A). In addition, we also observed increased p-Stat3 staining in SP cells over NSP cells, suggesting that SP cells may rely more heavily on Stat3 for survival.

Figure 3B:
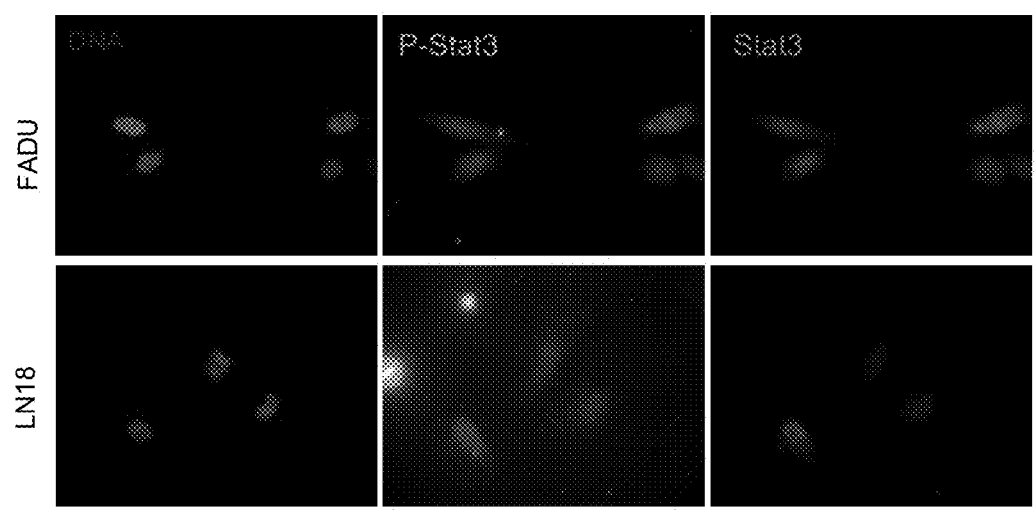
FIG. 3B shows that Stat3 is constitutively active in CD133$^+$ cells.

The status of Stat3 was also evaluated in CD133$^+$ cells isolated from FaDu human head and neck cancer cells and LN18 human glioblastoma cells. As shown in FIG. 3B, Stat3 are also constitutively active in these cells. Taken together, these data suggest Stat3 as a target that is particularly important for cancer stem cells.

Figure 4A:
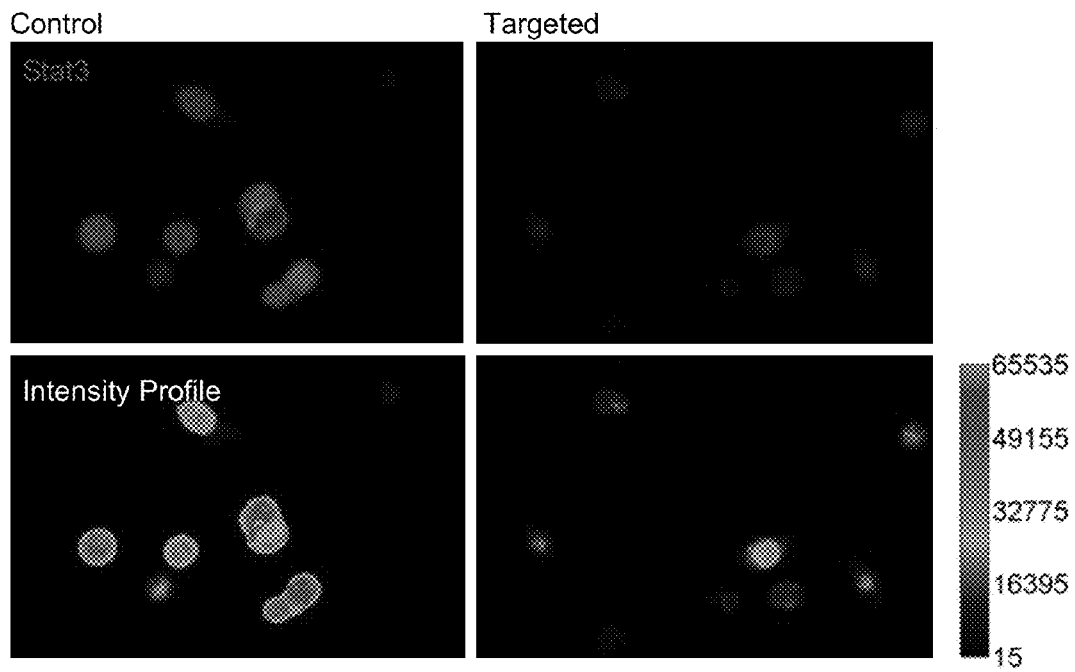
FIG. 4A shows the Stat3 knockdown in cancer stem cells.
Figure 4B:
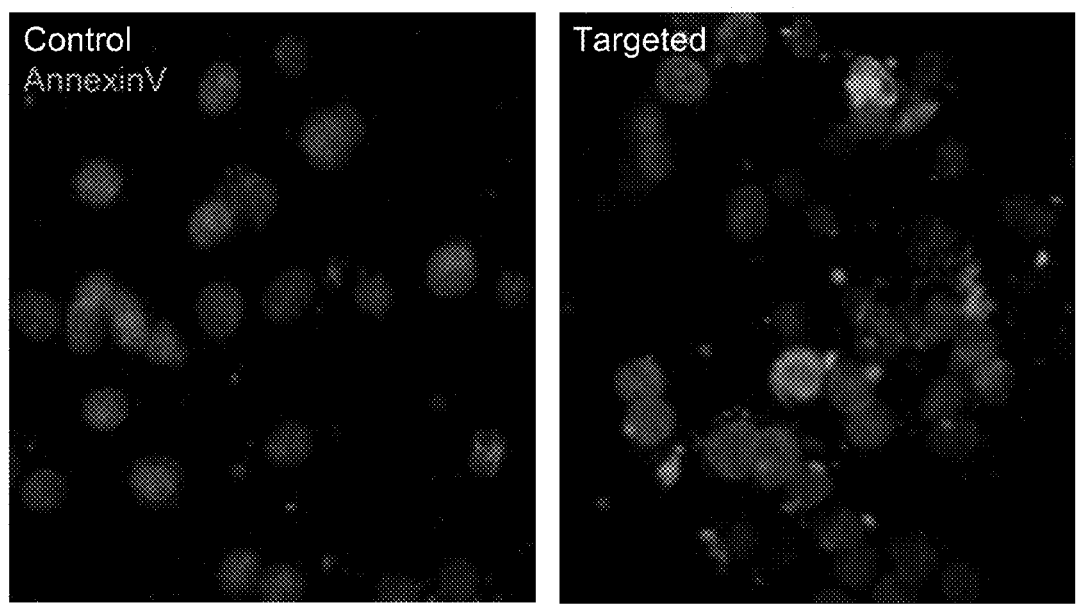
FIG. 4B shows that Stat3 knockdown in cancer stem cells induces apoptosis.

We next tested the effect of Stat3 knockdown in CSCs using TPIV®. Immunofluorescence analysis revealed that significant depletion of Stat3 could be achieved within 24 hours of infection (FIG. 4A) on freshly isolated CSCs (SP) and found that the majority of cells treated with Stat3 TPIV® underwent apoptosis within 24 hours of infection, whereas control TPIV® did not induce apoptosis to levels above control, uninfected cells (FIG. 4B). These data demonstrate that cancer stem cells depend upon Stat3 for survival.

Figure 5:
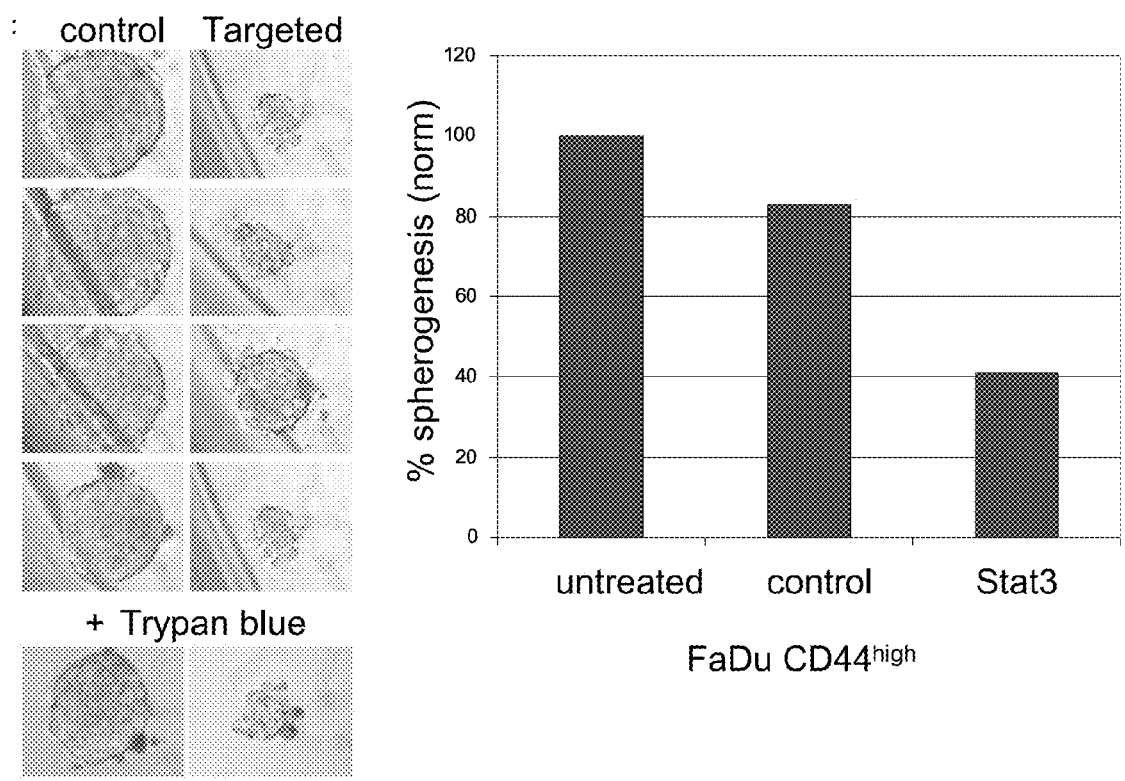
FIG. 5 shows that Stat3 knockdown in cancer stem cells inhibits cancer stem cell spherogenesis.

Knock Down Stat3 in CSCs Inhibits CSC Spherogenesis. CD44$^{high}$/CD24$^{low}$ FaDu or Hoeschst side population cancer stem cells were isolated by FACS, and cultured in ultra low attachment plates in cancer stem cell media (DMEM/F12, B27 Neurobasal supplement, 20 ng/mL EGF, 10 ng/mL FGF, 4 μg/mL insulin, and 0.4% BSA) to allow sphere formation. Primary spheres were collected, disaggregated with trypsin, and distributed to 96-well ultra low attachment plated prior to TPIV® treatment. Bacteria were administered at an MOI of 1000 for two hours before addition of antibiotic cocktail (penstrep, gentamycin, oflaxacin). Sphere formation was assessed after 10-14 days in culture. Representative sphere images were captured before (FIG. 5, left upper panels) or after the addition of trypan blue to identify dead cells (FIG. 5, left bottom panel). Relative spherogenesis was shown in the right panel of FIG. 5. The data clearly showed that Stat3 knockdown in cancer stem cells inhibits sphereogenesis, demonstrating that Stat3 is a key self-renewal factor of cancer stem cells.

Example 22

Identification of Compounds that Inhibit Stat3 Pathway Activity

Inhibition of Stat3 Transcription Activity.

Compounds were tested for their ability to inhibit Stat3 transcription activation activity in cells using a Stat3-luciferase (Stat3-luc) reporter construct. Cells transfected with Stat3-luc were cultured in reduced serum medium prior to addition of indicated compound for 30 minutes. Cells were then stimulated with 25 ng/ml oncostatin M (OSM) for 6 hours followed by detection of Stat3-luc reporter activity. Compounds tested in the Stat3 luciferase reporter assays and the results are summarized in Table 5.

TABLE 5

| Compound # | IC$_{50}$ in Stat3-Luc assays |
|---|---|
| 401 | ~0.25 μM |
| 416 | ~0.75 μM |
| 418 | ~0.75 μM |
| 402 | ~0.75 μM |
| 412 | ~0.75 μM |
| 410 | ~1 μM |
| 409 | ~2 μM |
| 408 | ~2 μM |
| 301 | ~2 μM |
| 407 | ~5 μM |

Inhibition of Stat3 DNA-Binding Activity.

Figure 6A:
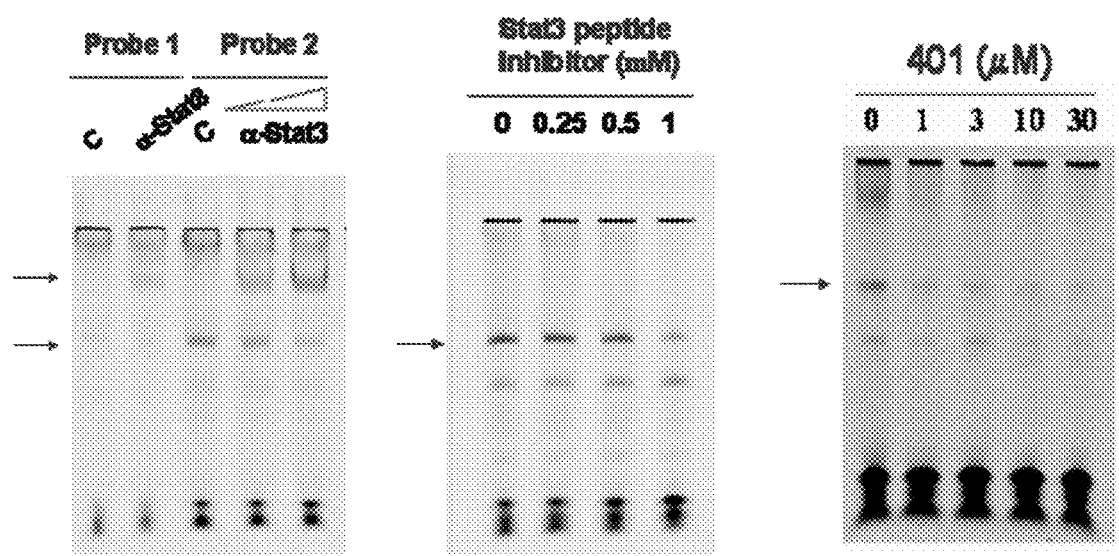
FIG. 6A shows that compound 401 inhibits Stat3 DNA-binding activity in nuclear extract.

Nuclear extracts from HeLa cells, which contain constitutively activated Stat3 as detected by phoshporylation at the tyrosine 705 residue, were used to perform Stat3 EMSAs to monitor Stat3 DNA binding activity. Nuclear extracts were incubated with indicated compound prior to incubation with IR700-labeled Stat3 consensus oligonucleotide. Binding of Stat3 to the oligonucleotide was monitored by gel electrophoresis and detection using a LiCor Odyssey infrared scanner. The Stat3 retarded band was identified and confirmed by supershift with the anti-Stat3 antibody (FIG. 6A, left panel) and dose-dependent inhibition with the Stat3 peptide (FIG. 6A, middle panel). Dose dependent inhibition of Stat3 DNA binding was observed following incubation of the labeled probe with compound 401 (FIG. 6A, right panel).

Figure 6B:
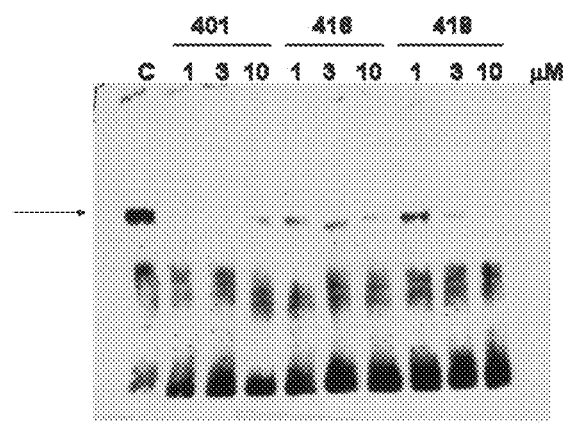
FIG. 6B shows that compounds 416 and 418 inhibits Stat3 DNA-binding activity in nuclear extract.

Additional compounds were tested in the EMSA assays and the results are shown in FIG. 6B and Table 6. To calculate the inhibition %, the density of the untreated Stat3 retarded band (control) was set as 100 and the inhibition % was the difference between the control and the relative DNA binding activity of the drug-treated samples. These data shows that the compounds of this invention can inhibit Stat3's DNA binding activity.

TABLE 6

| Compound | inhibition % | |
|---|---|---|
| | 1x MTT IC$_{50}$ | 3x MTT IC$_{50}$ |
| 418 | 39 | 63 |
| 420 | 47 | 63 |
| 302 | 6 | 25 |
| 106 | 26 | 51 |
| 202 | 50 | 46 |
| 402 | 29 | 57 |
| 301 | 20 | 26 |
| 406 | 16 | 34 |
| 103 | 98 | 26 |
| 304 | 25 | 55 |

Example 23

Identification of Compounds that Target Cancer Stem Cells

In order to test compounds for anti-CSC activity, freshly isolated CSCs (SW480 Hoechst SP cells or CD44$^{high}$ FaDu cells) were exposed to a dose range (30-0.117 µM) of compound for 48 h before examining cell viability by MTT assay. IC$_{50}$s were estimated by plotting the percentage of surviving cells. As shown in Table 7 and Table 8, the compounds of present invention can target cancer stem cells.

TABLE 7

| Compound | IC$_{50}$ (µM) | |
|---|---|---|
| | NSP | SP |
| 420 | 0.51 | 0.59 |
| 401 | 0.33 | 0.34 |
| 418 | 0.33 | 0.34 |
| 402 | 0.38 | 0.4 |
| 302 | 1.29 | 2.06 |
| 106 | 2 | 4.44 |

TABLE 8

| Compound | IC$_{50}$ (µM) | |
|---|---|---|
| | CD44$^{low}$ | CD44$^{high}$ |
| 202 | 2.25 | 2.4 |
| 304 | 2.49 | 2.41 |
| 302 | 3.68 | 0.68 |

REFERENCES

1. Yu, H. *Stat3: Linking oncogenesis with tumor immune evasion.* in *AACR 2008 Annual Meeting.* 2008. San Diego, Calif.
2. Pedranzini, L., A. Leitch, and J. Bromberg, *Stat3 is required for the development of skin cancer.* J Clin Invest, 2004. 114(5): p. 619-22.
3. Catlett-Falcone, R., et al., *Constitutive activation of Stat3 signaling confers resistance to apoptosis in human U266 myeloma cells.* Immunity, 1999. 10(1): p. 105-15.
4. Bromberg, J. F., et al., *Stat3 as an oncogene.* Cell, 1999. 98(3): p. 295-303.
5. Kanda, N., et al., *STAT3 is constitutively activated and supports cell survival in association with survivin expression in gastric cancer cells.* Oncogene, 2004. 23(28): p. 4921-9.
6. Schlette, E. J., et al., *Survivin expression predicts poorer prognosis in anaplastic large-cell lymphoma.* J Clin Oncol, 2004. 22(9): p. 1682-8.
7. Niu, G., et al., *Constitutive Stat3 activity up-regulates VEGF expression and tumor angiogenesis.* Oncogene, 2002. 21(13): p. 2000-8.
8. Xie, T. X., et al., *Stat3 activation regulates the expression of matrix metalloproteinase-2 and tumor invasion and metastasis.* Oncogene, 2004. 23(20): p. 3550-60.
9. Kortylewski, M., et al., *Inhibiting Stat3 signaling in the hematopoietic system elicits multicomponent antitumor immunity.* Nat Med, 2005. 11(12): p. 1314-21.
10. Burdelya, L., et al., *Stat3 activity in melanoma cells affects migration of immune effector cells and nitric oxide-mediated antitumor effects.* J Immunol, 2005. 174 (7): p. 3925-31.
11. Wang, T., et al., *Regulation of the innate and adaptive immune responses by Stat-3 signaling in tumor cells.* Nat Med, 2004. 10(1): p. 48-54.
12. Darnell, J. E., *Validating Stat3 in cancer therapy.* Nat Med, 2005. 11(6): p. 595-6.
13. Zhang, L., et al., *Intratumoral delivery and suppression of prostate tumor growth by attenuated Salmonella enterica serovar typhimurium carrying plasmid-based small interfering RNAs.* Cancer Res, 2007. 67(12): p. 5859-64.
14. Harris, T. J., et al., *Cutting edge: An in vivo requirement for STAT3 signaling in TH17 development and TH17-dependent autoimmunity.* J Immunol, 2007. 179(7): p. 4313-7.
15. Bonnet, D. and J. E. Dick, *Human acute myeloid leukemia is organized as a hierarchy that originates from a primitive hematopoietic cell.* Nat Med, 1997. 3(7): p. 730-7.
16. Hambardzumyan, D., M. Squatrito, and E. C. Holland, *Radiation resistance and stem-like cells in brain tumors.* Cancer Cell, 2006. 10(6): p. 454-6.
17. Baumann, M., M. Krause, and R. Hill, *Exploring the role of cancer stem cells in radioresistance.* Nat Rev Cancer, 2008. 8(7): p. 545-54.
18. Ho, M. M., et al., *Side population in human lung cancer cell lines and tumors is enriched with stem-like cancer cells.* Cancer Res, 2007. 67(10): p. 4827-33.
19. Wang, J., et al., *Identification of cancer stem cell-like side population cells in human nasopharyngeal carcinoma cell line.* Cancer Res, 2007. 67(8): p. 3716-24.
20. Haraguchi, N., et al., *Characterization of a side population of cancer cells from human gastrointestinal system.* Stem Cells, 2006. 24(3): p. 506-13.
21. Doyle, L. A. and D. D. Ross, *Multidrug resistance mediated by the breast cancer resistance protein BCRP (ABCG2).* Oncogene, 2003. 22(47): p. 7340-58.
22. Alvi, A. J., et al., *Functional and molecular characterisation of mammary side population cells.* Breast Cancer Res, 2003. 5(1): p. R1-8.
23. Frank, N. Y., et al., *ABCB5-mediated doxorubicin transport and chemoresistance in human malignant melanoma.* Cancer Res, 2005. 65(10): p. 4320-33.

24. Schatton, T., et al., *Identification of cells initiating human melanomas.* Nature, 2008. 451(7176): p. 345-9.
25. Kondo, T., T. Setoguchi, and T. Taga, *Persistence of a small subpopulation of cancer stem-like cells in the C6 glioma cell line.* Proc Natl Acad Sci USA, 2004. 101(3): p. 781-6.
26. Goodell, M. A., et al., *Isolation and functional properties of murine hematopoietic stem cells that are replicating in vivo.* J Exp Med, 1996. 183(4): p. 1797-806.
27. Al-Hajj, M., et al., *Prospective identification of tumorigenic breast cancer cells.* Proc Natl Acad Sci USA, 2003. 100(7): p. 3983-8.
28. Collins, A. T., et al., *Prospective identification of tumorigenic prostate cancer stem cells.* Cancer Res, 2005. 65(23): p. 10946-51.
29. Li, C., et al., *Identification of pancreatic cancer stem cells.* Cancer Res, 2007. 67(3): p. 1030-7.
30. Ma, S., et al., *Identification and characterization of tumorigenic liver cancer stem/progenitor cells.* Gastroenterology, 2007. 132(7): p. 2542-56.
31. Ricci-Vitiani, L., et al., *Identification and expansion of human colon-cancer-initiating cells.* Nature, 2007. 445 (7123): p. 111-5.
32. Singh, S. K., et al., *Identification of a cancer stem cell in human brain tumors.* Cancer Res, 2003. 63(18): p. 5821-8.
33. Bleau, A. M., et al., *New strategy for the analysis of phenotypic marker antigens in brain tumor-derived neurospheres in mice and humans.* Neurosurg Focus, 2008. 24(3-4): p. E28.
34. Libby, P., P. M. Ridker, and A. Maseri, *Inflammation and atherosclerosis.* Circulation, 2002. 105(9): p. 1135-43.
35. Stephens, J. W., et al., *A common functional variant in the interleukin-6 gene is associated with increased body mass index in subjects with type 2 diabetes mellitus.* Mol Genet Metab, 2004. 82(2): p. 180-6.
36. Cesari, M., et al., *Inflammatory markers and onset of cardiovascular events: results from the Health ABC study.* Circulation, 2003. 108(19): p. 2317-22.
37. Orshal, J. M. and R. A. Khalil, *Interleukin-6 impairs endothelium-dependent NO-cGMP-mediated relaxation and enhances contraction in systemic vessels of pregnant rats.* Am J Physiol Regul Integr Comp Physiol, 2004. 286(6): p. R1013-23.
38. Manolagas, S. C., *Role of cytokines in bone resorption.* Bone, 1995. 17(2 Suppl): p. 63S-67S.
39. Yaffe, K., et al., *Inflammatory markers and cognition in well-functioning African-American and white elders.* Neurology, 2003. 61(1): p. 76-80.
40. Watson, C. J. and W. R. Miller, *Elevated levels of members of the STAT family of transcription factors in breast carcinoma nuclear extracts.* Br J Cancer, 1995. 71(4): p. 840-4.
41. Song, J. I. and J. R. Grandis, *STAT signaling in head and neck cancer.* Oncogene, 2000. 19(21): p. 2489-95.
42. Song, L., et al., *Activation of Stat3 by receptor tyrosine kinases and cytokines regulates survival in human non-small cell carcinoma cells.* Oncogene, 2003. 22(27): p. 4150-65.
43. Savarese, T. M., et al., *Coexpression of oncostatin M and its receptors and evidence for STAT3 activation in human ovarian carcinomas.* Cytokine, 2002. 17(6): p. 324-34.
44. Toyonaga, T., et al., *Blockade of constitutively activated Janus kinase/signal transducer and activator of transcription-3 pathway inhibits growth of human pancreatic cancer.* Cancer Lett, 2003. 201(1): p. 107-16.
45. Corvinus, F. M., et al., *Persistent STAT3 activation in colon cancer is associated with enhanced cell proliferation and tumor growth.* Neoplasia, 2005. 7(6): p. 545-55.
46. Gao, B., et al., *Constitutive activation of JAK-STAT3 signaling by BRCA1 in human prostate cancer cells.* FEBS Lett, 2001. 488(3): p. 179-84.
47. Buettner, R., L. B. Mora, and R. Jove, *Activated STAT signaling in human tumors provides novel molecular targets for therapeutic intervention.* Clin Cancer Res, 2002. 8(4): p. 945-54.
48. Carson, W. E., *Interferon-alpha-induced activation of signal transducer and activator of transcription proteins in malignant melanoma.* Clin Cancer Res, 1998. 4(9): p. 2219-28.
49. Chen, C. L., et al., *Stat3 activation in human endometrial and cervical cancers.* Br J Cancer, 2007. 96(4): p. 591-9.
50. Lai, R., et al., *STAT3 is activated in a subset of the Ewing sarcoma family of tumours.* J Pathol, 2006. 208(5): p. 624-32.
51. Punjabi, A. S., et al., *Persistent activation of STAT3 by latent Kaposi's sarcoma-associated herpesvirus infection of endothelial cells.* J Virol, 2007. 81(5): p. 2449-58.
52. Schaefer, L. K., et al., *Constitutive activation of Stat3alpha in brain tumors: localization to tumor endothelial cells and activation by the endothelial tyrosine kinase receptor (VEGFR-2).* Oncogene, 2002. 21(13): p. 2058-65.
53. Puthier, D., R. Bataille, and M. Amiot, *IL-6 up-regulates mcl-1 in human myeloma cells through JAK/STAT rather than ras/MAP kinase pathway.* Eur J Immunol, 1999. 29(12): p. 3945-50.
54. Migone, T. S., et al., *Constitutively activated Jak-STAT pathway in T cells transformed with HTLV-I.* Science, 1995. 269(5220): p. 79-81.
55. Spiekermann, K., et al., *Constitutive activation of STAT transcription factors in acute myelogenous leukemia.* Eur J Haematol, 2001. 67(2): p. 63-71.
56. Epling-Burnette, P. K., et al., *Inhibition of STAT3 signaling leads to apoptosis of leukemic large granular lymphocytes and decreased Mcl-1 expression.* J Clin Invest, 2001. 107(3): p. 351-62.
57. Weber-Nordt, R. M., et al., *Constitutive activation of STAT proteins in primary lymphoid and myeloid leukemia cells and in Epstein-Barr virus (EBV)-related lymphoma cell lines.* Blood, 1996. 88(3): p. 809-16.
58. Sommer, V. H., et al., *In vivo activation of STAT3 in cutaneous T-cell lymphoma. Evidence for an antiapoptotic function of STAT3.* Leukemia, 2004. 18(7): p. 1288-95.
59. Lai, R., et al., *Signal transducer and activator of transcription-3 activation contributes to high tissue inhibitor of metalloproteinase-1 expression in anaplastic lymphoma kinase-positive anaplastic large cell lymphoma.* Am J Pathol, 2004. 164(6): p. 2251-8.
60. Fu, X. Y., *STAT3 in immune responses and inflammatory bowel diseases.* Cell Res, 2006. 16(2): p. 214-9.
61. Feldmann, M., F. M. Brennan, and R. N. Maini, *Role of cytokines in rheumatoid arthritis.* Annu Rev Immunol, 1996. 14: p. 397-440.
62. Krause, A., et al., *Rheumatoid arthritis synoviocyte survival is dependent on Stat3.* J Immunol, 2002. 169(11): p. 6610-6.
63. Pfitzner, E., et al., *The role of STATs in inflammation and inflammatory diseases.* Curr Pharm Des, 2004. 10(23): p. 2839-50.

64. Lovato, P., et al., *Constitutive STAT3 activation in intestinal T cells from patients with Crohn's disease.* J Biol Chem, 2003. 278(19): p. 16777-81.
65. Ishihara, K. and T. Hirano, *IL-6 in autoimmune disease and chronic inflammatory proliferative disease.* Cytokine Growth Factor Rev, 2002. 13(4-5): p. 357-68.
66. Ivashkiv, L. B. and I. Tassiulas, *Can SOCS make arthritis better?* J Clin Invest, 2003. 111(6): p. 795-7.
67. Sengupta, T. K., et al., *Activation of monocyte effector genes and STAT family transcription factors by inflammatory synovial fluid is independent of interferon gamma.* J Exp Med, 1995. 181(3): p. 1015-25.
68. Shouda, T., et al., *Induction of the cytokine signal regulator SOCS3/CIS3 as a therapeutic strategy for treating inflammatory arthritis.* J Clin Invest, 2001. 108(12): p. 1781-8.
69. Harada, T., et al., *Increased expression of STAT3 in SLE T cells contributes to enhanced chemokine-mediated cell migration.* Autoimmunity, 2007. 40(1): p. 1-8.
70. Simeone-Penney, M. C., et al., *Airway epithelial STAT3 is required for allergic inflammation in a murine model of asthma.* J Immunol, 2007. 178(10): p. 6191-9.
71. Hagler, M., Smith-Norowitz, T., Chice, S., Wallner, S., Viterbo, D., Mueller, C., Groos, R., Nowakowski, M., Schulze, R., Zenilman, M., *Sophorolipids decrease IgE production in U266 cells by downregulation of BSAP (Pax5), TLR-2, STAT3 and IL-6.* Journal of Allergy and Clinical Immunology, 2007. 119(S1): p. S263-S263.
72. Benkhart, E. M., et al., *Role of Stat3 in lipopolysaccharide-induced IL-10 gene expression.* J Immunol, 2000. 165(3): p. 1612-7.
73. Sano, S., et al., *Stat3 links activated keratinocytes and immunocytes required for development of psoriasis in a novel transgenic mouse model.* Nat Med, 2005. 11(1): p. 43-9.
74. Lim, C. P., et al., *Stat3 contributes to keloid pathogenesis via promoting collagen production, cell proliferation and migration.* Oncogene, 2006. 25(39): p. 5416-25.
75. Arany, I., et al., *Correlation between pretreatment levels of interferon response genes and clinical responses to an immune response modifier (Imiquimod) in genital warts.* Antimicrob Agents Chemother, 2000. 44(7): p. 1869-73.
76. Tefferi, A., *Classification, diagnosis and management of myeloproliferative disorders in the JAK2V617F era.* Hematology Am Soc Hematol Educ Program, 2006: p. 240-5.
77. Roder, S., et al., *STAT3 is constitutively active in some patients with Polycythemia rubra vera.* Exp Hematol, 2001. 29(6): p. 694-702.
78. Kim, O, S., et al., *JAK-STAT signaling mediates gangliosides-induced inflammatory responses in brain microglial cells.* J Biol Chem, 2002. 277(43): p. 40594-601.
79. Wyss-Coray, T., *Inflammation in Alzheimer disease: driving force, bystander or beneficial response?* Nat Med, 2006. 12(9): p. 1005-15.
80. Campbell, I. L., *Cytokine-mediated inflammation, tumorigenesis, and disease-associated JAK/STAT/SOCS signaling circuits in the CNS.* Brain Res Brain Res Rev, 2005. 48(2): p. 166-77.
81. Stelmasiak, Z., et al., *Interleukin-6 concentration in serum and cerebrospinal fluid in multiple sclerosis patients.* Med Sci Monit, 2000. 6(6): p. 1104-8.
82. Ponti, D., et al., *Isolation and in vitro propagation of tumorigenic breast cancer cells with stem/progenitor cell properties.* Cancer Res, 2005. 65(13): p. 5506-11.

The invention claimed is:

1. A compound of formula II,

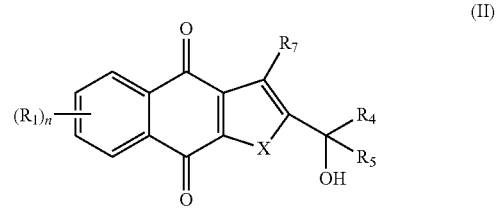

or an enantiomer, diastereomer, tautomer, or pharmaceutically acceptable salt thereof, wherein the symbols have the following meanings and are, for each occurrence, independently selected:

X is O or S;

$R_1$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, or $SR_a$;

$R_4$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, alkylaryl or substituted alkylaryl;

$R_5$ is hydrogen, alkyl or substituted alkyl, cycloalkyl or substituted cycloalkyl, aryl or substituted aryl, alkylaryl or substituted alkylaryl; optionally, $R_4$ and $R_5$ may be combined to form alkenyl or substituted alkenyl;

$R_7$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl; and n is 1-4, provided that at least one of $R_1$, $R_4$, $R_5$ and $R_7$ is aryl or substituted aryl.

2. The compound of claim 1, wherein the compound is:

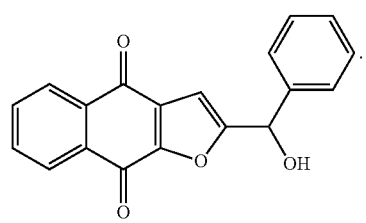 [SMILES: O=C1c2ccccc2C(=O)c2oc(C(O)c3ccccc3)cc21]

3. A compound of formula III,

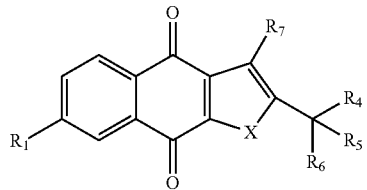

or an enantiomer, diastereomer, tautomer, or pharmaceutically acceptable salt thereof, wherein the symbols have the following meanings and are, for each occurrence, independently selected:

X is O or S;

$R_1$ is halogen;

$R_4$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, alkylaryl or substituted alkyl aryl;

$R_5$ is hydrogen, alkyl or substituted alkyl, cycloalkyl or substituted cycloalkyl, aryl or substituted aryl, alkylaryl or substituted alkylaryl; optionally, $R_4$ and $R_5$ may be combined to form alkenyl or substituted alkenyl;

$R_6$ is hydrogen, alkyl or substituted alkyl, $OR_a$, $OC(\!=\!O)R_a$, or $SR_a$;

$R_7$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, or $SR_a$; and $R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

4. A compound having the structure:

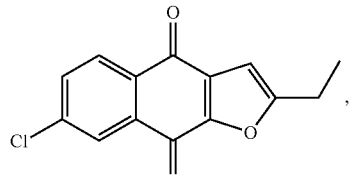

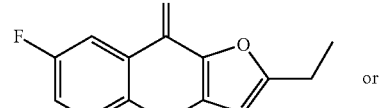
or

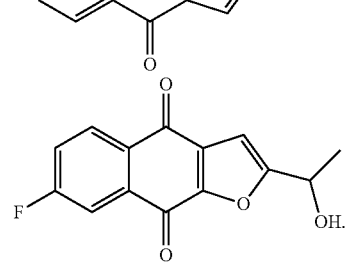

5. A pharmaceutical composition comprising a compound as claimed in claim 1, or an enantiomer, diastereomer, tautomer, or pharmaceutically acceptable salt thereof, and a pharmaceutically-acceptable excipient, carrier, or diluent.

6. A pharmaceutical composition comprising a compound as claimed in claim 3, or an enantiomer, diastereomer, tautomer, or pharmaceutically acceptable salt thereof, and a pharmaceutically-acceptable excipient, carrier, or diluent.

* * * * *